US011786122B2

(12) United States Patent
Berdahl et al.

(10) Patent No.: US 11,786,122 B2
(45) Date of Patent: Oct. 17, 2023

(54) APPARATUS AND METHODS TO ADJUST OCULAR BLOOD FLOW

(71) Applicant: Equinox Ophthalmic, Inc., Sioux Falls, SD (US)

(72) Inventors: John Berdahl, Sioux Falls, SD (US); George Tsai, Mission Viejo, CA (US); Hal Walbrink, Laguna Niguel, CA (US); Vance Michael Thompson, Sioux Falls, SD (US); Enrico Brambilla, Irvine, CA (US)

(73) Assignee: Equinox Ophthalmic, Inc., Newport Beach, CA (US)

( * ) Notice: Subject to any disclaimer, the term of this patent is extended or adjusted under 35 U.S.C. 154(b) by 33 days.

(21) Appl. No.: 17/168,670

(22) Filed: Feb. 5, 2021

(65) Prior Publication Data

US 2021/0153741 A1 May 27, 2021

Related U.S. Application Data

(63) Continuation of application No. PCT/US2019/045767, filed on Aug. 8, 2019.
(Continued)

(51) Int. Cl.
*A61B 3/16* (2006.01)
*A61B 5/00* (2006.01)

(52) U.S. Cl.
CPC .............. *A61B 3/16* (2013.01); *A61B 5/4836* (2013.01)

(58) Field of Classification Search
CPC ......... A61B 3/16; A61B 5/4836; A61B 5/021; A61B 5/024; A61B 5/031; A61B 3/1241;
(Continued)

(56) References Cited

U.S. PATENT DOCUMENTS 2,555,636 A  6/1951 Felts et al.
4,305,399 A 12/1981 Beale
(Continued)

FOREIGN PATENT DOCUMENTS

AU  2016311449      1/2019
AU  2019202196 A1   4/2019
(Continued)

OTHER PUBLICATIONS

"Cataract Surgery to Lower Intraocular Pressure", Middle East African Journal of Ophthalmology, 16 (3), (Sep. 2009), 1-5.
(Continued)

*Primary Examiner* — Richard G Louis
(74) *Attorney, Agent, or Firm* — Schwegman, Lundberg & Woessner, P.A.

(57) ABSTRACT

An apparatus to treat, inhibit, or prevent an eye condition in a patient can include a cover, sized and shaped to fit over an eye of a patient to define a cavity between the cover and an anterior surface of the eye when the cover is located over the patient eye. The apparatus can include a pressure source, in communication with the cavity, capable of applying non-ambient pressure in the cavity. The apparatus can include control circuitry, in communication with the pressure source, configured to vary non-ambient pressure applied to the cavity to affect a targeted pressure relationship between an indication of a first physiological pressure level and a second physiological pressure level associated with the eye of the patient.

20 Claims, 8 Drawing Sheets

Related U.S. Application Data

(60) Provisional application No. 62/716,669, filed on Aug. 9, 2018.

(58) Field of Classification Search
CPC .... A61B 5/02216; A61F 9/00; A61F 9/00781; A61F 9/02; A61H 9/0021; A61H 2205/024
See application file for complete search history.

(56) References Cited

U.S. PATENT DOCUMENTS

| | | |
|---|---|---|
| 4,387,707 A | 6/1983 | Polikoff |
| 4,604,087 A | 8/1986 | Joseph et al. |
| 4,724,843 A | 2/1988 | Fisher |
| 4,907,595 A | 3/1990 | Strauss |
| 5,201,312 A | 4/1993 | Schenck et al. |
| 5,300,020 A | 4/1994 | L'Esperance, Jr. |
| 5,338,291 A | 8/1994 | Speckman et al. |
| 5,523,808 A | 6/1996 | Kohayakawa |
| 5,601,548 A | 2/1997 | Smith et al. |
| 5,625,426 A | 4/1997 | Liu |
| 5,927,281 A | 7/1999 | Monteleone et al. |
| 5,951,477 A | 9/1999 | Ragaluskals et al. |
| 6,093,147 A | 7/2000 | Kontiola |
| 6,129,682 A | 10/2000 | Borchert et al. |
| 6,307,302 B1 | 10/2001 | Toda |
| 6,673,014 B2 | 1/2004 | Badchi et al. |
| 6,814,966 B1 | 11/2004 | Wax et al. |
| 7,122,007 B2 | 10/2006 | Querfurth |
| 7,137,952 B2 | 11/2006 | Leonardi |
| 7,331,666 B2 | 2/2008 | Swab et al. |
| 7,512,436 B2 | 3/2009 | Petty et al. |
| 7,850,638 B2 | 12/2010 | Theodore Coroneo |
| 8,408,204 B2 | 4/2013 | Lurie |
| 8,939,906 B2 | 1/2015 | Huang et al. |
| 8,998,810 B2 | 4/2015 | Kontiola et al. |
| 9,125,724 B2 | 9/2015 | Berdahl et al. |
| 9,168,172 B1 | 10/2015 | Berdahl |
| 9,173,564 B2 | 11/2015 | Choo et al. |
| 9,498,380 B2 | 11/2016 | Berdahl et al. |
| 10,029,009 B1 | 7/2018 | Berdahl |
| 10,154,926 B1 | 12/2018 | Berdahl et al. |
| 10,709,605 B1 | 7/2020 | Berdahl et al. |
| 10,842,376 B2 | 11/2020 | Berdahl et al. |
| 2002/0124843 A1 | 9/2002 | Skiba et al. |
| 2002/0193675 A1 | 12/2002 | Rathjen |
| 2003/0078486 A1 | 4/2003 | Klein et al. |
| 2003/0088260 A1 | 5/2003 | Smedley et al. |
| 2004/0111050 A1 | 6/2004 | Smedley et al. |
| 2004/0237969 A1 | 12/2004 | Fuller |
| 2004/0254517 A1 | 12/2004 | Quiroz-Mercado et al. |
| 2007/0123796 A1 | 5/2007 | Lenhardt et al. |
| 2007/0161875 A1 | 7/2007 | Epley |
| 2007/0282405 A1 | 12/2007 | Wong et al. |
| 2008/0086048 A1 | 4/2008 | Dupps et al. |
| 2008/0171953 A1 | 7/2008 | Mische |
| 2008/0221613 A1 | 9/2008 | Taske |
| 2008/0306429 A1 | 12/2008 | Shields et al. |
| 2009/0043365 A1 | 2/2009 | Friedland et al. |
| 2009/0270711 A1* | 10/2009 | Jarvin .............. A61B 3/16 600/398 |
| 2009/0306493 A1 | 12/2009 | Kontiola |
| 2010/0056935 A1 | 3/2010 | McKinley et al. |
| 2011/0022010 A1 | 1/2011 | Grenon et al. |
| 2011/0071458 A1 | 3/2011 | Rickard |
| 2011/0137182 A1 | 6/2011 | Bellezza et al. |
| 2012/0222201 A1 | 9/2012 | Dondero |
| 2013/0041245 A1 | 2/2013 | Cerboni |
| 2013/0072828 A1 | 3/2013 | Sweis et al. |
| 2013/0141690 A1 | 6/2013 | Taylor et al. |
| 2013/0144185 A1 | 6/2013 | Fuller et al. |
| 2013/0211285 A1 | 8/2013 | Fuller et al. |
| 2013/0215376 A1 | 8/2013 | Guo et al. |
| 2013/0238015 A1* | 9/2013 | Berdahl .............. A61B 5/6803 606/204.25 |
| 2013/0261530 A1 | 10/2013 | Yalamanchili |
| 2013/0274638 A1 | 10/2013 | Jennings et al. |
| 2014/0275935 A1 | 9/2014 | Walsh et al. |
| 2014/0378789 A1* | 12/2014 | McKinley .............. A61B 5/4041 600/301 |
| 2015/0094806 A1 | 4/2015 | Scholten |
| 2015/0164321 A1 | 6/2015 | Weibel et al. |
| 2015/0313761 A1 | 11/2015 | Berdahl et al. |
| 2017/0049620 A1 | 2/2017 | Berdahl et al. |
| 2017/0188860 A1 | 7/2017 | Fuller et al. |
| 2018/0279877 A1 | 10/2018 | Berdahl et al. |

FOREIGN PATENT DOCUMENTS

| | | |
|---|---|---|
| AU | 2019202196 | 9/2020 |
| AU | 2022211909 A1 | 9/2022 |
| CN | 102264277 | 11/2011 |
| CN | 103479326 | 1/2014 |
| CN | 203989163 | 12/2014 |
| CN | 108135738 | 6/2018 |
| CN | 113038869 A | 6/2021 |
| CN | 113842266 A | 12/2021 |
| DE | 19730735 A1 | 2/1999 |
| IN | 202117009018 A | 4/2021 |
| JP | H03193037 | 8/1991 |
| JP | 2013255791 | 12/2013 |
| JP | 2018527143 | 9/2018 |
| JP | 2021180879 A | 11/2021 |
| JP | 2021532920 A | 12/2021 |
| KR | 20180048749 | 5/2018 |
| KR | 102136640 | 7/2020 |
| WO | 2007012008 | 1/2007 |
| WO | 2007136993 | 11/2007 |
| WO | 2007139927 | 12/2007 |
| WO | 2010006180 | 1/2010 |
| WO | 2016071428 | 5/2016 |
| WO | 2017035406 | 3/2017 |
| WO | 2017156050 | 9/2017 |
| WO | 2018174835 | 9/2018 |
| WO | 2020033736 | 2/2020 |

OTHER PUBLICATIONS

"U.S. Appl. No. 14/800,018, Examiner Interview Summary dated Mar. 2, 2016", 3 pgs.

"U.S. Appl. No. 14/800,018, Notice of Allowance dated Jul. 20, 2016", 11 pgs.

"U.S. Appl. No. 15/345,053, Preliminary Amendment filed Nov. 16, 2016", 5 pgs.

"International Application Serial No. PCT US2016 048784, Invitation to Pay Additional Fees and Partial Search Report dated Nov. 28, 2016", 7 pgs.

"International Application Serial No. PCT US2016 048784, International Search Report dated Mar. 21, 2017", 9 pgs.

"International Application Serial No. PCT US2016 048784, Written Opinion dated Mar. 21, 2017", 10 pgs.

"U.S. Appl. No. 15/345,053, Supplemental Preliminary Amendment filed Aug. 21, 2017", 7 pgs.

"U.S. Appl. No. 15/688,016, Preliminary Amendment filed Aug. 29, 2017", 7 pgs.

"U.S. Appl. No. 15/688,043, Preliminary Amendment filed Aug. 29, 2017", 7 pgs.

"U.S. Appl. No. 15/688,016, Non Final Office Action dated Oct. 20, 2017", 16 pgs.

"EyeGatell Transcription", youtube, [Online]. Retrieved from the Internet: URL: https: www.youtube.com watch?v=v7oSLe-bLWo, (Accessed Nov. 3, 2017), 1 pg.

"U.S. Appl. No. 14/877,499, Non Final Office Action dated Nov. 27, 2017", 7 pgs.

"U.S. Appl. No. 15/688,016, Response filed Jan. 16, 2018 to Non Final Office Action dated Oct. 20, 2017", 9 pgs.

"U.S. Appl. No. 14/877,499, Response filed Feb. 14, 2018 to Non Final Office Action dated Nov. 27, 2017", 7 pgs.

"U.S. Appl. No. 15/688,043, Non Final Office Action dated Mar. 15, 2018", 11 pgs.

(56) References Cited

OTHER PUBLICATIONS

"International Application Serial No. PCT US2016 048784, International Preliminary Report on Patentability dated Mar. 8, 2018", 12 pgs.
"U.S. Appl. No. 14/877,499, Notice of Allowance dated Mar. 30, 2018", 5 pgs.
"U.S. Appl. No. 15/754,723, Preliminary Amendment filed Feb. 23, 2018", 8 pgs.
"U.S. Appl. No. 15/688,016, Final Office Action dated May 15, 2018", 11 pgs.
"U.S. Appl. No. 15/688,016, Response filed Jun. 12, 2018 to Final Office Action dated May 15, 2018", 10 pgs.
"U.S. Appl. No. 15/912,872, Non Final Office Action dated Jun. 8, 2018", 13 pgs.
"U.S. Appl. No. 15/688,043, Response filed Jun. 15, 2018 to Non Final Office Action dated Mar. 15, 2018", 11 pgs.
"U.S. Appl. No. 15/912,872, Response filed Jul. 9, 2018 to Non Final Office Action dated Jun. 8, 2018", 15 pgs.
"U.S. Appl. No. 15/688,043, Notice of Allowance dated Jul. 16, 2018", 9 pgs.
"U.S. Appl. No. 15/688,016, Advisory Action dated Jul. 25, 2018", 4 pgs.
"Australian Application Serial No. 2016311449, First Examination Report dated Jul. 27, 2018", 4 pgs.
"U.S. Appl. No. 15/688,016, Response filed Aug. 15, 2018 to Advisory Action dated Jul. 25, 2018", 9 pgs.
"U.S. Appl. No. 15/688,043, Corrected Notice of Allowability dated Sep. 13, 2018", 3 pgs.
"U.S. Appl. No. 15/688,043, Corrected Notice of Allowability dated Sep. 28, 2018", 3 pgs.
"U.S. Appl. No. 15/688,016, Non Final Office Action dated Oct. 5, 2018", 12 pgs.
"Canadian Application Serial No. 2,998,477, Examiner's Rule 30(2) Requisition dated Oct. 5, 2018", 3 pgs.
Alexander, David J., "Risk of Spaceflight-Induced Intracranial Hypertension and Vision Alterations", Evidence Report—Version 1.0, (Jul. 12, 2012), 109 pgs.
Allin, David, "Laboratory Testing of the Pressio Intracranial Pressure Monitor", Neurosurgery, vol. 62, vol. 5, [Online]. Retrieved from the Internet: URL: www.neurosurgery-online.com, (May 2008), 1158-1161.
Araci, Ismail E., "An implantable microfuidic device for self-monitoring of intraocular pressure", nature medicine, vol. 20, No. 9—Technical Reports, (Sep. 2014), 1074-1080.
Berdahl, John P., "Intracranial Pressure in Primary Open Angle Glaucoma, Normal Tension Glaucoma, and Ocluar Hypertension: A Case-Control Study", IOVS, vol. 49, No. 12, (Dec. 2008), 5412-5418.
Berdahl, John P., "Systemic Parameters Associated With Cerebrospinal Fluid Pressure", J Glaucoma, vol. 22, No. 5, Suppl 1, [Online]. Retrieved from the Internet: URL: www.glaucomajournal.com, (Jul. 2013), S17-818.
Berdahl, John P., "Body Mass Index Has a Linear Relationship with Cerebrospinal Fluid Pressure", IOVS, vol. 53, No. 3, (Mar. 2012), 1422-1427.
Chowdhury, "Intracranial Pressure and its Relationship to Glaucoma: Current Understanding and Future Directions", Med Hypothesis Discov Innov Ophthalmol, 4(3), (2015), 1 pg.
Costa, Vital P., "Ocular perfusion pressure in glaucoma", Acta Ophthalmologica, (2014), e252-e266.
Fleischman, David, "Cerebrospinal Fluid Pressure Decreases with Older Age", PLOS One, vol. 7, Issue 12, [Online]. Retrieved from the Internet: URL: www.plosone.org, (Dec. 2012), 1-9.
Fleischman, David, "The role of cerebrospinal fluid pressure in glaucoma and other ophthalmic diseases: A review", Saudi Journal of Ophthalmology, 27, (2013), 97-106.
Hillen, Mark, "In Practice (VIIP: A Space Odyssey)", The Ophthalmologist, vol. 11, (Sep. 2014), 6 pgs.

Jacks, A. S., "Spontaneous retinal venous pulsation: aetiology and significance", J Neurol Neurosurg Psychiatry; 74, [Online]. Retrieved from the Internet: URL:www.jnnp.com, (2002), 7-9.
Lehman, "Experimental effect of intracranial hypertension upon intraocular pressure", J Neurosurg, 36(1):60-6, (Jan. 1972), 1 pg.
Morgan, William H., "Retinal venous pulsation: Expanding our understanding and use of this enigmatic phenomenon", Progress in Retinal and Eye Research xxx, (2016), 1-26.
Muenster, Stefan, "The Ability of Nitric Oxide to Lower Intraocular Pressure Is Dependent on Guanylyl Cyclase", Investigative Ophthalmology and Visual Science, vol. 58, No. 11, (Sep. 2017), 4826-4835.
Sajjadi, "The Relation between Intracranial and Intraocular Pressures: Study of 50 Patients", Ann Neurol, (2006), 867-870.
Young, Joshua, "ASFH CSF Pressure and Glaucoma (Guest: John P. Berdahl, M.D.)", As Seen From Here: 198 (Podcast—iTunes) (Transcribed) Run time: 15:14 Minutes, (Jul. 8, 2008), 5 pgs.
"U.S. Appl. No. 13/790,048, Non Final Office Action dated Jun. 24, 2014", 9 pgs.
"U.S. Appl. No. 13/790,048, Response filed Sep. 24, 2014 to Non Final Office Action dated Jun. 24, 2014", 16 pgs.
"U.S. Appl. No. 12/380,239, Final Office Action dated Oct. 8, 2014", 12 pgs.
"U.S. Appl. No. 12/380,239, Response filed Jan. 7, 2015 to Final Office Action dated Oct. 8, 2014", 20 pgs.
"U.S. Appl. No. 13/790,048, Final Office Action dated Feb. 5, 2015", 13 pgs.
"U.S. Appl. No. 12/380,239, Non Final Office Action dated Feb. 6, 2015", 9 pgs.
"U.S. Appl. No. 13/790,048, Response filed Apr. 2, 2015 to Final Office Action dated Feb. 5, 2015", 11 pgs.
"U.S. Appl. No. 13/790,048, Notice of Allowance dated May 4, 2015", 12 pgs.
"U.S. Appl. No. 12/380,239, Response filed May 4, 2015 to Non Final Office Action dated Feb. 6, 2015", 13 pgs.
"U.S. Appl. No. 12/380,239, Notice of Allowance dated Jun. 19, 2015", 5 pgs.
"U.S. Appl. No. 12/380,239, Restriction Requirement dated Jun. 2, 2011", 5 pgs.
"U.S. Appl. No. 12/380,239, Response filed Jul. 1, 2011 to Restriction Requirement dated Jun. 2, 2011", 3 pgs.
"U.S. Appl. No. 12/380,239, Non Final Office Action dated Jul. 14, 2011", 15 pgs.
"U.S. Appl. No. 12/380,239, Response filed Oct. 12, 2012 to Non Final Office Action dated Jul. 14, 2011", 12 pgs.
"U.S. Appl. No. 12/380,239, Response filed Apr. 16, 2014 to Non Final Office Action dated Jul. 14, 2011", 12 pgs.
"U.S. Appl. No. 12/380,239, Amendment filed May 8, 2014", 11 pgs.
"U.S. Appl. No. 12/380,239, Notice of Non-Compliant Amendment dated Jun. 20, 2014", 2 pgs.
"U.S. Appl. No. 12/380,239, Response to Notice of Non-Compliant Amendment dated Jun. 24, 2014", 14 pgs.
"U.S. Appl. No. 12/380,239, Corrected Notice of Allowance dated Jul. 8, 2015", 3 pgs.
"U.S. Appl. No. 14/800,018, Preliminary Amendment filed Jul. 28, 2015", 5 pgs.
"U.S. Appl. No. 14/800,018, Non Final Office Action dated Sep. 28, 2015", 15 pgs.
"U.S. Appl. No. 14/877,499, Preliminary Amendment filed Oct. 8, 2015", 5 pgs.
"U.S. Appl. No. 14/800,018 Response filed Jan. 15, 2016 to Non-Final Office Action dated Sep. 28, 2015", 20 pgs.
Araci, Ismail E., "An implantable microfluidic device for self-monitoring of intraocular pressure", Nature Medicine, vol. 20, No. 9, (Sep. 2014), 1074-1080.
Berdahl, "Cerebrospinal fluid pressure is decreased in primary open-angle glaucoma", Ophthalmology 115(5), (May 2008), 763-768.
Berdahl, J. P., "Intracranial pressure and glaucoma", Curr Opin Ophthalmol (2), (Mar. 2010), 1 pg.

(56) References Cited

OTHER PUBLICATIONS

Berdahl, J. P., "The translaminar pressure gradient in sustained zero gravity,idiopathic intracranial hypertension, and glaucoma", PubMed 79(6), (Dec. 2012), 1 pg.
Berdahl, John, "Cerebrospinal Fluid Pressure and Glaucoma", Glaucoma Today, (Oct. 2009), 14-18.
Berdahl, John P., "Recovery of Corneal Hysteresis after Reduction of Intraocular Pressure in Chronic Primary Angle-Closure Glaucoma", American Journal of Ophthalmology—Correspondence, (Oct. 2009), 623-624.
Berdahl, John P., "The translaminar pressure gradient in sustained zero gravity, idiopathic inracranial hypertension and glaucoma", Medical Hypotheses 79, (2012), 719-724.
Berdahl, John P., "Intracranial pressure and glaucoma", Current Opinion in Ophthalmology 21-, (2010), 106-111.
Digre, Kathleen, "Not so benign intracranial hypertension", MBJ, 326(7390), (Mar. 22, 2003), 613-614.
Fleischman, David, "Increasing intraocular pressure as treatment for papilledema", Experimental Eye Research 115, (2013), 278.
Goel, Manik, "Aqueous Humor Dynamics: A Review", The Open Ophthalmology Journal, [Online]. Retrieved from the Internet: URL: http: www.ncbi.nlm.nih.gov pmc articles PMC3032230, (2010), 52-59.
Goldman, Robert M., "The Effects of Oscillating Inversion on Systemic Blood Pressure, Pulse Intraocular Pressure, and Central Retinal Arterial Pressure", The Physician and Sportsmedicine, vol. 13, No. 3, (Mar. 1985), 93-96.
Hayreh, Sohan Singh, "Cerebrospinal fluid pressure and glaucomatous optic disc cupping (response to Berdahl and colleagues)", Graefes Arch Clin Exp Opthtalmol, 247, (2009), 1291-1294.
Huberman, Andrew, "Managing Glaucoma: Beyond Intraocular Pressure. 2011", Review of Opthalmology, [Online]. Retrieved from the Internet: URL: : http: www.reviewofophthalmology.com continuing_education tabviewtest lessonid 107804 , (Sep. 2011), 17 pgs.
Jonas, Jost B., "Anatomic Relationship between Lamina Cribosa, Intraocular Space, and Cerebrospinal Fluid Space", Investigative Ophthalmology and Visual Science, vol. 44, No. 12, (Dec. 2003), 5189-5195.
Jung, Jong Jin, "Analysis of the Causes of Optic-Disc Swelling", Korean J Ophthalmol, 25 (1), (2011), 33-36.
Zhang, Zheng, "Glaucoma and the Role of Cerebrospinal Fluid Dynamics", Investigative Ophthalmology and Visual Sciences, (2015), 6632.
Kent, Christopher, "IOP: Managing the Fluctuation Factor", Review of Ophthalmology, [Online]. Retrieved from the Internet: URL:http: www.reviewofophfhalmology.com content i 1533 c 28662 dnnprintmode true ?skinsrc=[l]skinsrp2010 pageprintandcontainersre= [l]containers rp2010 blank, (Jun. 13, 2011), 6 pgs.
Kwon, "A Patient's Guide to Glaucoma", sections 5A and 6B, (2006), 4 pgs.
Parsa, C F, "Spontaneous venous pulsations should be monitored during glaucoma therapy", Br J Ophthalmol, 86 (10), (Oct. 2002), 1187.
Samuelson, T W, "Intracranial pressure may play significant role in glaucoma", Ocular Surgery News US Edition, (Oct. 25, 2008), 3 pgs.
Siaudvytyte, Lina, "Update in intracranial pressure evaluation methods and translaminar pressure gradient role in glaucoma", ACTA Opththmalologica, 93, (2015), 9-15.
Wostyn, Peter, "Glaucoma and the Role of Cerebrospinal Fluid Dynamics", Investigative Ophthalmology and Visual Sciences, (2015), 6630.
Wuthrich, U. W., "Postural change and intraocular pressure in glaucomatous eyes", Brit. J. Ophthal. 60, (1976), 111-114.
Xie, Xiaobin, "Noninvasive intracranial pressure estimation by orbital subarachnoid space measurement: the Beijing Intracranial and Intraocular Pressure (ICOP) study", Critical Care, 17:R162, [Online]. Retrieved from the Internet: URL: http: www.ncbi.nlm.nih.gov pmc articles PMC4056099 pdf cc12841.pdf, (2013), 12 pgs.
Yeoh, Ronald, "Hydrorupture of the posterior capsule in femtosecond-laser cataract surgery", J Cataract Refract Surg, vol. 38, (Apr. 2012), 730-731.
"Canadian Application Serial No. 2,998,477, Response filed Jun. 9, 2020 to Office Action dated Feb. 17, 2020", 18 pgs.
"U.S. Appl. No. 15/688,016, Corrected Notice of Allowability dated Jun. 15, 2020", 3 pgs.
"Brazilian Application Serial No. 1120180038385, Office Action dated Jun. 24, 2020", w English Translation, 5 pgs.
"U.S. Appl. No. 15/754,723, Response filed Jul. 15, 2020 to Non Final Office Action dated Apr. 17, 2020", 11 pgs.
"U.S. Appl. No. 15/345,053, Final Office Action dated Jul. 24, 2020", 11 pgs.
"European Application Serial No. 16763632.3, Response filed Jul. 22, 2020 to Communication Pursuant to Article 94(3) EPC dated Mar. 26, 2020", 14 pgs.
"U.S. Appl. No. 15/754,723, Notice of Allowance dated Jul. 29, 2020", 5 pgs.
"U.S. Appl. No. 15/912,872, Examiner Interview Summary dated Jul. 30, 2020", 3 pgs.
"U.S. Appl. No. 15/912,8/2, Response filed Jul. 30, 2020 to Non Final Office Action dated Apr. 30, 2020", 10 pgs.
"Canadian Application Serial No. 2,998,477, Office Action dated Aug. 7, 2020", 6 pgs.
"Japanese Application Serial No. 2018-529509, Notification of Reasons for Refusal dated Aug. 11, 2020", w English translation, 9 pgs.
"Australian Application Serial No. 2019202196, Response filed Aug. 19, 2020 to First Examination Report dated Apr. 22, 2020", 19 pgs.
"U.S. Appl. No. 15/754,723, Supplemental Notice of Allowability dated Sep. 10, 2020", 2 pgs.
"U.S. Appl. No. 15/345,053, Response filed Sep. 23, 2020 to Final Office Action dated Jul. 24, 2020", 10 pgs.
"Chinese Application Serial No. 201680056279.2, Response filed Sep. 27, 2020 to Office Action dated May 22, 2020", w English Claims, 19 pgs.
"U.S. Appl. No. 15/912,872, Notice of Allowance dated Oct. 5, 2020", 8 pgs.
"European Application Serial No. 16763632.3, Communication Pursuant to Article 94(3) EPC dated Sep. 28, 2020", 5 pgs.
"U.S. Appl. No. 15/345,053, Advisory Action dated Oct. 14, 2020", 3 pgs.
"Brazilian Application Serial No. 1120180038385, Response filed Oct. 5, 2020 to Office Action dated Jun. 24, 2020", w English Claims, 129 pgs.
"U.S. Appl. No. 15/754,723, Supplemental Notice of Allowability dated Oct. 21, 2020", 2 pgs.
"Korean Application Serial No. 10-2020-7020680, Notice of Preliminary Rejection dated Oct. 5, 2020", w English Translation, 9 pgs.
"Canadian Application Serial No. 2,998,477, Response filed Nov. 9, 2020 to Office Action dated Aug. 7, 2020", 12 pgs.
"Japanese Application Serial No. 2018-529509, Response filed Nov. 11, 2020 to Notification of Reasons for Refusal dated Aug. 11, 2020", w English Claims, 7 pgs.
"U.S. Appl. No. 17/077,205, Preliminary Amendment filed Nov. 25, 2020", 6 pgs.
"Korean Application Serial No. 10-2020-7020680, Response filed Dec. 7, 2020 to Notice of Preliminary Rejection dated Oct. 5, 2020", w English claims, 8 pgs.
"Japanese Application Serial No. 2018-529509, Notification of Reasons for Refusal dated Dec. 15, 2020", w English translation, 8 pgs.
"U.S. Appl. No. 15/912,872, 312 Amendment filed Jan. 5, 2021", 3 pgs.
"Indian Applicaiton Serial No. 201817010073, First Examination Report dated Dec. 11, 2020", w English Translation, 7 pgs.
"Australian Application Serial No. 2019319942, First Examination Report dated Aug. 9, 2021", 3 pgs.
"Australian Application Serial No. 2019319942, Response filed Apr. 22, 2022 to First Examination Report dated Aug. 9, 2021", 163 pgs.

(56) References Cited

OTHER PUBLICATIONS

"Australian Application Serial No. 2020286245, First Examination Report dated Apr. 8, 2022", 4 pgs.
"Canadian Application Serial No. 3,109,225, Office Action dated Feb. 10, 2022", 5 pgs.
"Eurasian Application Serial No. 19759175.3, Response to Communication pursuant to Rules 161(1) and 162 EPC filed Sep. 13, 2021", 16 pgs.
"European Application Serial No. 16763632.3, Communication Pursuant to Article 94(3) EPC dated Jun. 17, 2021", 4 pgs.
"European Application Serial No. 16763632.3, Response filed Dec. 27, 2021 to Communication Pursuant to Article 94(3) EPC dated Jun. 17, 2021", 14 pgs.
"Indian Application Serial No. 202117009018, First Examination Report dated Jan. 24, 2022", 7 pgs.
"Indian Application Serial No. 202117009018, Response filed Mar. 16, 2022 to First Examination Report dated Jan. 24, 2022", w/ English claims, 110 pgs.
"Japanese Application Serial No. 2021-505948, Notification of Reasons for Refusal dated May 10, 2022", w/ English translation, 7 pgs.
"Korean Application Serial No. 10-2020-7020680, Response filed Jul. 22, 2021 to Final Office Action dated Apr. 23, 2021", w/ English claims, 12 pgs.
Luo, et al., "Ocular blood flow autoregulation mechanisms and methods", Eye Center, Renmin Hospital of Wuhan University, Wuhan, China; vol. 2015, (Oct. 21, 2015).
"U.S. Appl. No. 15/754,723, Supplimental Preliminary Amendment filed Nov. 15, 2018", 8 pgs.
"U.S. Appl. No. 15/688,043, Corrected Notice of Allowability dated Nov. 20, 2018", 2 pgs.
"U.S. Appl. No. 15/912,872, Final Office Action dated Nov. 28, 2018", 14 pgs.
"U.S. Appl. No. 15/688,016, Response filed Dec. 31, 2018 to Non Final Office Action dated Oct. 5, 2018", 11 pgs.
"U.S. Appl. No. 15/912,872, Response filed Jan. 4, 2019 to Final Office Action dated Nov. 28, 2018", 10 pgs.
"U.S. Appl. No. 15/688,016, Examiner Interview Summary dated Dec. 31, 2018", 3 pgs.
"European Application Serial No. 16763632.3, Response filed Nov. 1, 2018 to Communication Pursuant to Rules 161(1) and 162 EPC dated Apr. 25, 2018", w English Claims, 11 pgs.
"U.S. Appl. No. 15/345,053, Non Final Office Action dated Feb. 15, 2019", 11 pgs.
"Canadian Application Serial No. 2,998,477, Response Filed Mar. 18, 2019 to Examiner's Rule 30(2) Requisition dated Oct. 5, 2018", 23 pgs.
"U.S. Appl. No. 15/688,016, Final Office Action dated Mar. 25, 2019".
"European Application Serial No. 16763632.3, Communication Pursuant to Article 94(3) EPC dated Apr. 4, 2019", 5 pgs.
"U.S. Appl. No. 15/345,053, Response filed May 13, 2019 to Non Final Office Action dated Feb. 15, 2019", 9 pgs.
"U.S. Appl. No. 15/688,016, Response filed May 28, 2019 to Final Office Action dated Mar. 25, 2019", 10 pgs.
"U.S. Appl. No. 15/912,872, Non Final Office Action dated Jun. 6, 2019", 13 pgs.
"Canadian Application Serial No. 2,998,477, Office Action dated Jun. 25, 2019", 3 pgs.
"Korean Application Serial No. 10-2018-7008191, Notice of Preliminary Rejection dated Jul. 10, 2019", w English Translation, 15 pgs.
"U.S. Appl. No. 15/345,053, Final Office Action dated Aug. 22, 2019", 11 pgs.
"U.S. Appl. No. 15/688,016, Non Final Office Action dated Aug. 29, 2019", 12 pgs.
"U.S. Appl. No. 15/912,872, Examiner Interview Summary dated Aug. 30, 2019", 3 pgs.
"European Application Serial No. 16763632.3, Response Filed Aug. 14, 2019 to Communication Pursuant to Article 94(3) EPC dated Apr. 4, 2019", 15 pgs.
"U.S. Appl. No. 15/912,872, Response filed Sep. 6, 2019 to Non-Final Office Action dated Jun. 6, 2019", 12 pgs.
"Korean Application Serial No. 10-2018-7008191, Response Filed Sep. 4, 2019 to Notice of Preliminary Rejection dated Jul. 10, 2019", w English Claims, 26 pgs.
"Chinese Application Serial No. 201680056279.2, Office Action dated Sep. 12, 2019", w English translation, 21 pgs.
"U.S. Appl. No. 15/345,053, Response filed Oct. 22, 2019 to Final Office Action dated Aug. 22, 2019", 10 pgs.
"European Application Serial No. 16763632.3, Communication Pursuant to Article 94(3) EPC dated Oct. 18, 2019", 4 pgs.
"Eye-Related Intrabody Pressure Identification and Modification", (Oct. 28, 2019), 3.
"U.S. Appl. No. 15/688,016, Response filed Nov. 19, 2019 to Non Final Office Action dated Aug. 29, 2019", 10 pgs.
"U.S. Appl. No. 15/688,016, Examiner Interview Summary dated Nov. 25, 2019", 3 pgs.
"U.S. Appl. No. 15/345,053, Advisory Action dated Dec. 2, 2019", 3 pgs.
"International Application Serial No. PCT US2019 045767, International Search Report dated Nov. 26, 2019", 5 pgs.
"International Application Serial No. PCT US2019 045767, Written Opinion dated Nov. 26, 2019", 7 pgs.
"U.S. Appl. No. 15/912,872, Final Office Action dated Dec. 12, 2019", 13 pgs.
"Canadian Application Serial No. 2,998,477, Response filed Dec. 9, 2019 to Office Action dated Jun. 25, 2019", 19 pgs.
"Biosensor", Merriam-Webster dictionary, [Online]. Retrieved from the Internet: https: www.merriam-webster.com dictionary biosensor, (Jan. 6, 2020), 2 pgs.
"U.S. Appl. No. 15/345,053, Non Final Office Action dated Jan. 13, 2020", 12 pgs.
"Chinese Application Serial No. 201680056279.2, Response filed Jan. 16, 2020 to Office Action dated Sep. 12, 2019", w English Claims, 18 pgs.
"Korean Application Serial No. 10-2018-7008191, Final Office Action dated Jan. 23, 2020", w English Translation, 5 pgs.
"U.S. Appl. No. 15/912,872, Response filed Feb. 12, 2020 to Final Office Action dated Dec. 12, 2019", 9 pgs.
"U.S. Appl. No. 15/688,016, Notice of Allowance dated Feb. 20, 2020", 7 pgs.
"Canadian Application Serial No. 2,998,477, Office Action dated Feb. 17, 2020", 6 pgs.
"U.S. Appl. No. 15/912,872, Advisory Action dated Mar. 11, 2020", 3 pgs.
"U.S. Appl. No. 15/912,872, Response filed Mar. 20, 2020 to Advisory Action dated Mar. 11, 2020", 9 pgs.
"European Application Serial No. 16763632.3, Response filed Feb. 27, 2020 to Communication Pursuant to Article 94(3) EPC dated Oct. 18, 2019", 11 pgs.
"Korean Application Serial No. 10-2018-7008191, Response filed Mar. 25, 2020 to Final Office Action dated Jan. 23, 2020", w English Claims, 12 pgs.
"European Application Serial No. 16763632.3, Communication Pursuant to Article 94(3) EPC dated Mar. 26, 2020", 4 pgs.
"U.S. Appl. No. 15/754,723, Non Final Office Action dated Apr. 17, 2020", 8 pgs.
"Australian Application Serial No. 2019202196, First Examination Report dated Apr. 22, 2020", 5 pgs.
"U.S. Appl. No. 15/912,872, Non Final Office Action dated Apr. 30, 2020", 17 pgs.
"U.S. Appl. No. 15/345,053, Response filed Apr. 13, 2020 to Non Final Office Action dated Jan. 13, 2020", 9 pgs.
"Chinese Application Serial No. 201680056279.2, Office Action dated May 22, 2020", w English Translation, 19 pgs.
"Canadian Application Serial No. 3,109,225, Examiner's Rule 86(2) Requisition Report dated Sep. 8, 2022", 3 pgs.
"Canadian Application Serial No. 3,109,225, Response Filed Jun. 10, 2022 to Office Action dated Feb. 10, 2022", 36 pgs.

(56) References Cited

OTHER PUBLICATIONS

"Japanese Application Serial No. 2021-128035, Notification of Reasons for Rejection dated Jul. 5, 2022", w/ English Translation, 7 pgs.

"Japanese Application Serial No. 2021-505948, Notification of Reasons for Refusal dated Nov. 29, 2022", w/ English translation, 11 pgs.

"Japanese Application Serial No. 2021-505948, Response filed Jul. 25, 2022 to Notification of Reasons for Refusal dated May 10, 2022", w/ English claims, 9 pgs.

"Canadian Application Serial No. 3,109,225, Response filed Jan. 9, 2023 to Examiner's Rule 86(2) Requisition Report dated Sep. 8, 2022", 9 pgs.

"Korean Application Serial No. 10-2021-7006949, Notice of Preliminary Rejection dated Jan. 27, 2023", w English Translation, 12 pgs.

"Japanese Application Serial No. 2021-505948, Response filed Feb. 2, 2023 to Notification of Reasons for Refusal dated Nov. 29, 2022", w English claims, 8 pgs.

"Korean Application Serial No. 10-2021-7006949, Response filed May 26, 2023 to Notice of Preliminary Rejection dated Jan. 27, 2023", w English claims, 22 pgs.

\* cited by examiner

COEXTRUDED OR BONDED TUBING

COEXTRUDED COAXIAL TUBING

TUBE WITHIN A TUBE

APPARATUS AND METHODS TO ADJUST OCULAR BLOOD FLOW

CLAIM OF PRIORITY

This patent application is a continuation of International Application No. PCT/US2019/045767, entitled "APPARATUS AND METHODS TO ADJUST OCULAR BLOOD FLOW," filed Aug. 8, 2019, which claims the benefit of priority of U.S. Provisional Patent Application Ser. No. 62/716,669 to John Berdahl entitled "Eye and Blood Pressure Based Eye Treatment," filed on Aug. 9, 2018 which is hereby incorporated by reference in entirety.

BACKGROUND

Intraocular pressure (IOP) is an important physiological parameter in the field of ophthalmology. Controlled variation of IOP can be used to assess and treat eye conditions.

Morris U.S. Pat. No. 5,032,111 mentions an apparatus for controlling IOP during closed wound intraocular surgery including a gas pump, a liquid infusate reservoir, and an ocular surgical infusion instrument.

Denninghoff U.S. Pat. No. 6,701,169 mentions a method of determining the autoregulatory status of the eye including obtaining a first measurement of retinal blood vessels, administering a preselected stimulus, obtaining a second measurement of blood vessels in response to the stimulus, and determining a ratio.

Kuenen U.S. Publication No. 20160128587 mentions a method for measuring intracranial pressure (ICP) including detecting an SVP, identifying the orientation of the head where the SVP start to occur or stop occurring, and using the identified orientation of the head to determine the ICP in the subject.

SUMMARY

Glaucoma is a leading cause of blindness in the world today. Mechanical causes, such as elevated intraocular pressure (IOP), are widely recognized as important risk factors in glaucoma. However, as seen in normal-tension glaucoma, the disease can progress even in the absence of excessive TOP. Vascular impairment, such as a lack of blood flow to ocular tissues, is a fundamentally different cause of glaucoma and can play an important role in the etiology and pathogenesis of disease as well as other eye conditions.

The present inventors have recognized, among other things, that there is a need in the art for apparatus and methods to adjust blood flow, such as the volume of blood flow, in a patient eye. The apparatus and methods described herein can adjust blood flow in the eye to treat, inhibit, and prevent eye conditions including glaucoma through enhanced ocular perfusion. The apparatus and methods can further be used for purposes of patient evaluation, such as the assessment of ocular autoregulation capability and non-invasive estimation of cerebrospinal fluid pressure.

An apparatus can include a cover, sized and shaped to fit over a patient eye to define a cavity between the cover and an anterior surface of the eye. The apparatus can include a pressure source, in communication with the cavity and configured to adjust fluid pressure in the cavity. The apparatus can include control circuitry, in communication with the pressure source, configured to receive an indication of a blood vessel parameter from a blood vessel in the eye and process the received indication to adjust fluid pressure in the cavity based on the received indication.

An overview of certain non-limiting aspects of the present subject matter is provided below.

Aspect 1 can include or use subject matter (such as an apparatus, a system, a device, a method, a means for performing acts, or a device readable medium including instructions that, when performed by the device, can cause the device to perform acts, or an article of manufacture), such as can include or use an apparatus to adjust ocular blood flow in a patient eye. The apparatus can comprise a cover, sized and shaped to fit over the eye to define a cavity between the cover and an anterior surface of the eye, a pressure source, in communication with the cavity, configured to adjust fluid pressure in the cavity, and control circuitry, in communication with the pressure source, configured to adjust fluid pressure in the cavity to regulate ocular blood flow toward a target level.

Aspect 2 can include or use or can optionally be combined with the subject matter of Aspect 1 to optionally include or use an apparatus wherein the control circuitry is configured to receive an indication of a blood vessel parameter associated with an ocular blood vessel to adjust fluid pressure in the cavity based at least in part on the received indication.

Aspect 3 can include or use or can optionally be combined with the subject matter of one or any combination of Aspects 1 or 2 to optionally include or use an apparatus wherein the control circuitry is configured to process the received indication.

Aspect 4 can include or use or can optionally be combined with the subject matter of one or any combination of Aspects 1 through 3 to optionally include or use an apparatus wherein the indication of the blood vessel parameter includes an indication of ocular blood flow in the ocular blood vessel.

Aspect 5 can include or use or can optionally be combined with the subject matter of one or any combination of Aspects 1 through 4 to optionally include or use an apparatus including a blood flow sensor configured to sense the indication of blood flow from the blood vessel in the eye.

Aspect 6 can include or use or can optionally be combined with the subject matter of one or any combination of Aspects 1 through 5 to optionally include or use an apparatus wherein the control circuitry is configured to receive an indication of TOP in the eye and the indication of blood flow to adjust fluid pressure in the cavity based at least in part on the received indications.

Aspect 7 can include or use or can optionally be combined with the subject matter of one or any combination of Aspects 1 through 6 to optionally include or use an apparatus including an TOP sensor, configured to sense the indication of IOP in the eye.

Aspect 8 can include or use or can optionally be combined with the subject matter of one or any combination of Aspects 1 through 7 to optionally include or use an apparatus wherein the control circuitry is configured to receive an indication of systemic blood pressure in the patient and the indications of blood flow and IOP to adjust fluid pressure in the cavity based at least in part on the received indications.

Aspect 9 can include or use or can optionally be combined with the subject matter of one or any combination of Aspects 1 through 8 to optionally include or use an apparatus including a blood pressure sensor, configured to sense the indication of systemic blood pressure in the patient.

Aspect 10 can include or use or can optionally be combined with the subject matter of one or any combination of Aspects 1 through 9 to optionally include or use an apparatus wherein the control circuitry is configured to adjust fluid pressure in the cavity toward a target blood flow level based on a relationship between the received indications.

Aspect 11 can include or use or can optionally be combined with the subject matter of one or any combination of Aspects 1 through 10 to optionally include or use an apparatus wherein the control circuitry is configured to adjust the cavity pressure to adjust blood flow toward a target blood flow level in the patient eye based on a relationship between the received indications.

Aspect 12 can include or use or can optionally be combined with the subject matter of one or any combination of Aspects 1 through 11 to optionally include or use an apparatus wherein the relationship between the received indications includes an ocular perfusion pressure (OPP) level.

Aspect 13 can include or use or can optionally be combined with the subject matter of one or any combination of Aspects 1 through 12 to optionally include or use an apparatus wherein the control circuitry is configured to process the indication of blood flow to provide an ocular autoregulation (OA) value.

Aspect 14 can include or use or can optionally be combined with the subject matter of one or any combination of Aspects 1 through 13 to optionally include or use an apparatus wherein the target level includes a target OPP graph-point level and the control circuitry is configured to provide the OA value as an OA ordered pair including the target OPP graph-point level and the indication of blood flow corresponding to the target OPP graph-point level.

Aspect 15 can include or use or can optionally be combined with the subject matter of one or any combination of Aspects 1 through 14 to optionally include or use an apparatus wherein the control circuitry is configured to process at least two OA ordered pairs to calculate an OA index.

Aspect 16 can include or use or can optionally be combined with the subject matter of one or any combination of Aspects 1 through 15 to optionally include or use an apparatus wherein the OA index includes a slope of a best-fit line between at least two OA ordered pairs.

Aspect 17 can include or use or can optionally be combined with the subject matter of one or any combination of Aspects 1 through 16 to optionally include or use an apparatus wherein the control circuitry is configured to adjust pressure in the cavity toward affecting a target SVP state based at least in part on the received indication of blood flow to estimate CSFP level in the patient.

Aspect 18 can include or use or can optionally be combined with the subject matter of one or any combination of Aspects 1 through 17 to optionally include or use an apparatus including an imaging sensor configured to sense the indication of the blood vessel caliber from the blood vessel in the eye.

Aspect 19 can include or use or can optionally be combined with the subject matter of one or any combination of Aspects 1 through 18 to optionally include or use an apparatus including an SVP sensor configured to sense the indication of the vessel caliber from the blood vessel in the eye.

Aspect 20 can include or use or can optionally be combined with the subject matter of one or any combination of Aspects 1 through 19 to optionally include or use an apparatus wherein the control circuitry is configured to receive an indication of systemic blood pressure including an indication of systolic and diastolic blood pressure level, and wherein the control circuitry is configured to capture a first image of the blood vessel parameter corresponding to the systolic blood pressure level and a second image of the blood vessel parameter corresponding to the diastolic blood pressure level.

Aspect 21 can include or use or can optionally be combined with the subject matter of one or any combination of Aspects 1 through 20 to optionally include or use an apparatus wherein the control circuitry is configured to receive an indication of IOP associated with the indication of blood flow to provide an indication of CSFP at the target SVP state.

Aspect 22 can include or use or can optionally be combined with the subject matter of one or any combination of Aspects 1 through 21 to optionally include or use an apparatus including a pressure sensor configured to sense the indication of IOP associated with the received indications.

Aspect 23 can include or use or can optionally be combined with the subject matter of one or any combination of Aspects 1 through 22 to optionally include or use an apparatus wherein the pressure sensor includes an IOP sensor to sense the indication of TOP.

Aspect 24 can include or use or can optionally be combined with the subject matter of one or any combination of Aspects 1 through 23 to optionally include or use an apparatus wherein the pressure sensor includes a cavity pressure sensor to sense an estimate of the indication of TOP.

Aspect 25 can include or use or can optionally be combined with the subject matter of one or any combination of Aspects 1 through 24 to optionally include or use an apparatus wherein the indication of the blood vessel parameter includes the blood vessel caliber, and wherein the control circuitry is configured to calculate a vessel caliber factor to adjust fluid pressure in the cavity toward affecting an associated target SVP state to estimate CSFP level in the patient based at least in part on the vessel caliber factor, the vessel caliber factor defined as a ratio of a first vessel caliber value corresponding to the first image at a first pressure in a patient cardiac cycle and a second vessel caliber value corresponding to the second image at a second pressure in the patient cardiac cycle.

Aspect 26 can include or use or can optionally be combined with the subject matter of one or any combination of Aspects 1 through 25 to optionally include or use an apparatus wherein the first pressure in the patient cardiac cycle includes the systolic blood pressure level and the second pressure in the patient cardiac cycle includes the diastolic blood pressure level.

Aspect 27 can include or use or can optionally be combined with the subject matter of one or any combination of Aspects 1 through 26 to optionally include or use an apparatus wherein the indication of the blood vessel parameter includes a vessel shape characteristic for a blood vessel cross-section, the vessel shape characteristic indicating a relationship between a major axis of the blood vessel and a minor axis of the blood vessel, and wherein the control circuitry is configured to calculate a vessel characteristic factor to adjust fluid pressure in the cavity toward affecting an associated target SVP state to estimate CSFP level in the patient based at least in part on the vessel characteristic factor, the vessel characteristic factor indicating a relationship of a first vessel shape characteristic corresponding to the first image at a first pressure in a patient cardiac cycle and a second vessel shape characteristic corresponding to the second image at a second pressure in the patient cardiac cycle.

Aspect 28 can include or use or can optionally be combined with the subject matter of one or any combination of Aspects 1 through 27 to optionally include or use an apparatus wherein the first pressure in the patient cardiac cycle includes the systolic blood pressure level and the second pressure in the patient cardiac cycle includes the diastolic blood pressure level.

Aspect 29 can include or use subject matter (such as an apparatus, a system, a device, a method, a means for performing acts, or a device readable medium including instructions that, when performed by the device, can cause the device to perform acts, or an article of manufacture), or can optionally be combined with the subject matter of one or any combination of Aspects 1 through 28 to optionally include or use a method using an apparatus. The apparatus can comprise a cover, sized and shaped to fit over the eye to define a cavity between the cover and an anterior surface of the eye, a pressure source, in communication with the cavity, configured to adjust fluid pressure in the cavity, and control circuitry, in communication with the pressure source, configured to adjust fluid pressure in the cavity to regulate ocular blood flow toward a target level. The method can include a step of receiving the indication of a blood vessel parameter in a patient eye with control circuitry. The method can include a step of using the control circuitry based on the received indication to adjust fluid pressure in a cavity defined between the cover and an anterior surface of the eye.

Aspect 30 can include or use or can optionally be combined with the subject matter of one or any combination of Aspects 1 through 29 to optionally include or use the method wherein receiving the indication of the blood vessel parameter includes receiving an indication of blood flow in the blood vessel.

Aspect 31 can include or use or can optionally be combined with the subject matter of one or any combination of Aspects 1 through 30 to optionally include or use the method comprising displaying the received indication to the user through the GUI to allow the user to adjust fluid pressure in the cavity based on the indication of the blood vessel parameter.

Aspect 32 can include or use or can optionally be combined with the subject matter of one or any combination of Aspects 1 through 31 to optionally include or use the method wherein processing the received indication includes calculating the difference between the received indication and a target blood vessel parameter value.

Aspect 33 can include or use or can optionally be combined with the subject matter of one or any combination of Aspects 1 through 32 to optionally include or use the method wherein processing includes generating a feedback signal configured to adjust the pressure source based on the received indication.

Aspect 34 can include or use or can optionally be combined with the subject matter of one or any combination of Aspects 1 through 33 to optionally include or use the method wherein generating the feedback signal includes generating the feedback signal configured to adjust the pressure source toward a target blood flow level in the patient eye.

Aspect 35 can include or use or can optionally be combined with the subject matter of one or any combination of Aspects 1 through 34 to optionally include or use the method comprising receiving an indication of intraocular pressure (IOP) in the eye and an indication of systemic blood pressure in the patient with the control circuitry.

Aspect 36 can include or use or can optionally be combined with the subject matter of one or any combination of Aspects 1 through 35 to optionally include or use the method wherein processing the received indication includes calculating an indication of ocular perfusion pressure (OPP) based on the received indications of TOP and systemic blood pressure.

Aspect 37 can include or use or can optionally be combined with the subject matter of one or any combination of Aspects 1 through 36 to optionally include or use the method wherein the control circuitry includes a graphical user interface (GUI) configured to convey an indication of OPP to a user, and wherein processing includes displaying the indication OPP to the user through the GUI to allow the user to manually adjust fluid pressure in the cavity based on the indication of OPP.

Aspect 38 can include or use or can optionally be combined with the subject matter of one or any combination of Aspects 1 through 37 to optionally include or use the method wherein processing the received indication includes generating a feedback signal configured to adjust the pressure source based on the indication of OPP.

Aspect 39 can include or use or can optionally be combined with the subject matter of one or any combination of Aspects 1 through 38 to optionally include or use the method wherein processing the received indication includes forming an ocular autoregulation (OA) value including an OA ordered pair.

Aspect 40 can include or use or can optionally be combined with the subject matter of one or any combination of Aspects 1 through 39 to optionally include or use the method wherein processing the received indication includes calculating an ocular autoregulation (OA) index based on at least two OA values.

Aspect 41 can include or use or can optionally be combined with the subject matter of one or any combination of Aspects 1 through 40 to optionally include or use the method wherein calculating an OA index includes calculating a slope of a best-fit line between the at least two OA values.

Aspect 42 can include or use or can optionally be combined with the subject matter of one or any combination of Aspects 1 through 41 to optionally include or use the method comprising receiving an indication of pressure associated with the patient eye including at least one of fluid pressure in the cavity or an indication of IOP in the eye.

Aspect 43 can include or use or can optionally be combined with the subject matter of one or any combination of Aspects 1 through 42 to optionally include or use the method wherein receiving an indication of a blood vessel parameter includes receiving an indication of vessel caliber and processing the received indication includes determining an indication of SVP state.

Aspect 44 can include or use or can optionally be combined with the subject matter of one or any combination of Aspects 1 through 43 to optionally include or use the method wherein the control circuitry includes a graphical user interface (GUI) configured to convey an indication of SVP state to a user, and wherein processing includes displaying the indication of SVP state to the user through the GUI to allow the user to manually adjust fluid pressure in the cavity based on the indication of SVP state.

Aspect 45 can include or use or can optionally be combined with the subject matter of one or any combination of Aspects 1 through 44 to optionally include or use the method wherein processing the received indication includes generating a feedback signal configured to adjust the pressure source based on the indication of SVP state.

Aspect 46 can include or use or can optionally be combined with the subject matter of one or any combination of Aspects 1 through 45 to optionally include or use the method wherein generating the feedback signal includes generating the feedback signal configured to adjust the pressure source toward a target SVP state.

Aspect 47 can include or use or can optionally be combined with the subject matter of one or any combination of Aspects 1 through 46 to optionally include or use the method wherein generating the feedback signal includes generating the feedback signal to adjust the pressure source from an SVP ON state to an SVP OFF state.

Aspect 48 can include or use or can optionally be combined with the subject matter of one or any combination of Aspects 1 through 47 to optionally include or use the method wherein generating the feedback signal includes generating the feedback signal to adjust the pressure source from an SVP OFF state to an SVP ON state.

Aspect 49 can include or use or can optionally be combined with the subject matter of one or any combination of Aspects 1 through 48 to optionally include or use the method wherein processing the received indication includes displaying the indication of pressure associated with the patient eye at the target SVP state as an estimate of CSFP level in the patient.

Aspect 50 can include or use or can optionally be combined with the subject matter of one or any combination of Aspects 1 through 49 to optionally include or use the method wherein receiving the indication of the blood vessel parameter includes visualizing a blood vessel characteristic.

Aspect 51 can include or use or can optionally be combined with the subject matter of one or any combination of Aspects 1 through 50 to optionally include or use the method wherein visualizing a blood vessel parameter includes imaging a blood vessel parameter with an imaging sensor.

Aspect 52 can include or use or can optionally be combined with the subject matter of one or any combination of Aspects 1 through 51 to optionally include or use the method wherein visualizing a blood vessel parameter includes sensing an indication of SVP with an SVP sensor.

Aspect 53 can include or use or can optionally be combined with the subject matter of one or any combination of Aspects 1 through 52 to optionally include or use the method wherein using the control circuitry includes increasing cavity pressure above ambient pressure toward a target SVP state to estimate CSFP in the patient.

Aspect 54 can include or use or can optionally be combined with the subject matter of one or any combination of Aspects 1 through 53 to optionally include or use the method wherein using the control circuitry includes decreasing cavity pressure below ambient pressure toward a target SVP state to estimate CSFP in the patient.

Aspect 55 can include or use subject matter (such as an apparatus, a system, a device, a method, a means for performing acts, or a device readable medium including instructions that, when performed by the device, can cause the device to perform acts, or an article of manufacture), or can optionally be combined with the subject matter of one or any combination of Aspects 1 through 54 to optionally include or use a method of using an apparatus. The apparatus can comprise a cover, sized and shaped to fit over the eye to define a cavity between the cover and an anterior surface of the eye, a pressure source, in communication with the cavity, configured to adjust fluid pressure in the cavity, and control circuitry, in communication with the pressure source, configured to adjust fluid pressure in the cavity to regulate ocular blood flow toward a target level. The method can include a step of forming a cavity between a patient eye and a cover, the cover sized and shaped to fit over the eye. The method can include a step of adjusting fluid pressure in the cavity to affect a target SVP state to estimate CSFP in the patient.

Aspect 56 can include or use or can optionally be combined with the subject matter of one or any combination of Aspects 1 through 55 to optionally include or use the method wherein adjusting fluid pressure in the cavity includes increasing fluid pressure in the cavity to affect a transition from an initial SVP state to the target SVP state.

Aspect 57 can include or use or can optionally be combined with the subject matter of one or any combination of Aspects 1 through 56 to optionally include or use the method wherein adjusting fluid pressure in the cavity includes increasing fluid pressure in the cavity to affect a transition from an initial SVP state to the target SVP state.

Aspect 58 can include or use or can optionally be combined with the subject matter of one or any combination of Aspects 1 through 57 to optionally include or use the method wherein adjusting fluid pressure in the cavity includes decreasing fluid pressure in the cavity to affect a transition from an initial SVP state to the target SVP state.

Aspect 59 can include or use or can optionally be combined with the subject matter of one or any combination of Aspects 1 through 58 to optionally include or use the method wherein adjusting fluid pressure in the cavity includes visualizing an SVP state of an ocular blood vessel with an imaging sensor.

Aspect 60 can include or use or can optionally be combined with the subject matter of one or any combination of Aspects 1 through 59 to optionally include or use the method wherein adjusting fluid pressure in the cavity includes detecting an TOP in the patient eye corresponding to a transition from an initial SVP to the target SVP state to estimate CSFP in the patient.

Aspect 61 can include or use or can optionally be combined with the subject matter of one or any combination of Aspects 1 through 60 to optionally include or use the method wherein adjusting fluid pressure in the cavity includes decreasing fluid pressure in the cavity to affect a transition from an initial SVP state to the target SVP state.

Aspect 62 can include or use or can optionally be combined with the subject matter of one or any combination of Aspects 1 through 61 to optionally include or use the method wherein adjusting fluid pressure in the cavity includes visualizing an SVP state of an ocular blood vessel with an imaging sensor.

Aspect 63 can include or use or can optionally be combined with the subject matter of one or any combination of Aspects 1 through 62 to optionally include or use the method wherein adjusting fluid pressure in the cavity includes detecting an TOP in the patient eye corresponding to a transition from an initial SVP to the target SVP state to estimate CSFP in the patient.

Aspect 64 can include or use subject matter (such as an apparatus, a system, a device, a method, a means for performing acts, or a device readable medium including instructions that, when performed by the device, can cause the device to perform acts, or an article of manufacture), such as can include or use an apparatus to adjust ocular blood flow in a patient eye. The apparatus can comprise a cover, sized and shaped to fit over the eye to define a cavity between the cover and an anterior surface of the eye, a pressure source, in communication with the cavity, configured to adjust fluid pressure in the cavity, and control circuitry, in communication with the pressure source, configured to receive an indication of pressure associated with the patient eye and an indication of systemic blood pressure (BP) and process the received indications to adjust fluid pressure in the cavity based at least in part on at least one of the received indications.

Aspect 65 can include or use or can optionally be combined with the subject matter of one or any combination of Aspects 1 through 64 to optionally include or use an apparatus wherein the indication of pressure associated with the eye includes at least one of an indication of fluid pressure in the cavity or an indication of intraocular pressure (IOP) in the eye.

Aspect 66 can include or use or can optionally be combined with the subject matter of one or any combination of Aspects 1 through 65 to optionally include or use an apparatus wherein the indication of fluid pressure is sensed with a pressure sensor and the indication of IOP is sensed with an IOP sensor.

Aspect 67 can include or use or can optionally be combined with the subject matter of one or any combination of Aspects 1 through 66 to optionally include or use an apparatus wherein the indication of systemic BP is sensed with a BP sensor.

Aspect 68 can include or use or can optionally be combined with the subject matter of one or any combination of Aspects 1 through 67 to optionally include or use an apparatus wherein the control circuitry includes a graphical user interface (GUI) configured to convey an indication of pressure associated with the eye to a user, and wherein processing includes displaying the indication of pressure to the user through the GUI to allow the user to manually adjust fluid pressure in the cavity based on the indication of pressure.

Aspect 69 can include or use or can optionally be combined with the subject matter of one or any combination of Aspects 1 through 68 to optionally include or use an apparatus wherein the control circuitry includes a graphical user interface (GUI) configured to convey an indication of pressure associated with the eye to a user, and wherein processing includes displaying the indication of IOP to the user through the GUI to allow the user to manually adjust fluid pressure in the cavity based on the indication of IOP.

Aspect 70 can include or use or can optionally be combined with the subject matter of one or any combination of Aspects 1 through 69 to optionally include or use an apparatus wherein processing includes displaying to the user through the GUI a first indication of IOP level at a first indication of systemic BP level and a second indication of IOP level at a second indication of system BP level to allow the user to manually adjust fluid pressure in the cavity based on at least one of the first or second indication of IOP.

Aspect 71 can include or use or can optionally be combined with the subject matter of one or any combination of Aspects 1 through 70 to optionally include or use an apparatus wherein the first indication of system BP level includes an indication of systolic BP in a patient cardiac cycle and the second indication of system BP level includes an indication of diastolic BP in the patient cardiac cycle.

Aspect 72 can include or use or can optionally be combined with the subject matter of one or any combination of Aspects 1 through 71 to optionally include or use an apparatus wherein the control circuitry is configured to adjust fluid pressure in the cavity toward a target level.

Aspect 73 can include or use or can optionally be combined with the subject matter of one or any combination of Aspects 1 through 72 to optionally include or use an apparatus wherein the control circuitry is configured to adjust fluid pressure in the cavity toward a target IOP level in the eye.

Aspect 74 can include or use or can optionally be combined with the subject matter of one or any combination of Aspects 1 through 73 to optionally include or use an apparatus wherein the control circuitry is configured to adjust fluid pressure in the cavity toward a target level based on a relationship between the received indications.

Aspect 75 can include or use or can optionally be combined with the subject matter of one or any combination of Aspects 1 through 74 to optionally include or use an apparatus wherein the control circuitry is configured process an indication of ocular perfusion pressure (OPP) level in the patient eye and adjust fluid pressure in the cavity toward a target ocular perfusion pressure (OPP) level based on the indication of OPP.

Each of these non-limiting examples can stand on its own or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
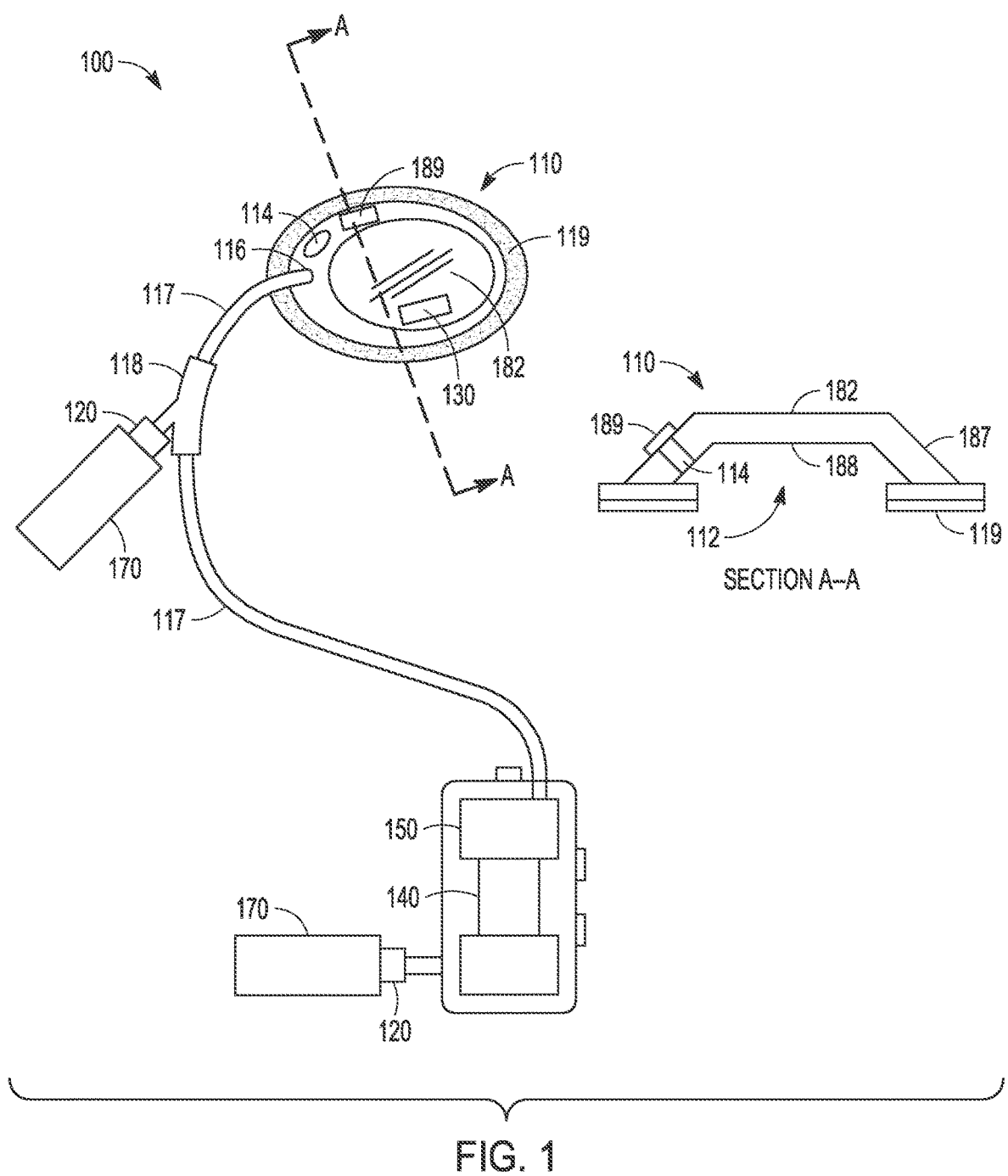
FIG. 1 shows an example of an apparatus to control an environment over a patient eye.

FIG. 1 shows an example of an apparatus 100, such as to control an environment over a patient eye. In at least one example, the patient eye can include an organ of the visual system, such as an anterior surface of the patient eye. The apparatus 100 can include a cover 110, a fluid regulator 120, a sensor 130, control circuitry 140, and a pressure source 150.

The cover 110 can be sized and shaped to surround the patient eye and be spaced from the eye, such as without contacting the eye including the anterior surface of the eye. The cover 110 can be sized and shaped to surround and cover both patient eyes, such as the left eye and the right eye of a patient. In an example, the cover 110 can include a mask, such as a cover 110 similar in shape and function to a diving or snorkeling mask. The cover 110 can include a lens portion 182 to allow a patient to see outward through the cover 110 or to allow observation of the eye, such as exterior structures of the eye including the cornea or intraocular structures of the eye including the retina, inward through the cover 110. The lens portion 182 can serve as a corrective lens for the patient, such as to correct an astigmatism of the eye. The lens portion 182 can include a lens blank, such as an A8 lens blank, that can be shaped as a prescription lens for the patient, such as to correct for refractive error in the eye. The lens portion 182 can include a replaceable lens portion 182, such as a first lens portion in the apparatus 100 can be interchanged with a second lens portion, such as to change the lens magnification presented to the patient. In an example, lens magnification can be selected to allow for examination of the intraocular space of the eye including assessment of the retina and the choroid, such as for at least one of diagnostic or treatment purposes. The lens magnification can be selected to enhance the examination of the eye, such as to focus the lens portion 182 to enhance visualization of a portion of the eye. The inner surface of the lens portion 182 can be treated, such as with an anti-fog coating to prevent condensation from obscuring the view of the patient.

The cover 110 can define an enclosed cavity 112, such as when the cover 110 is placed over the eye and against the patient. The cavity 112 can define an enclosed cavity 112 over both eyes, such as when the cover 110 includes a mask located over left and right patient eyes. In an example, a peripheral edge of the cover 110 can be placed over the eye, such as the peripheral edge can contact at least a portion of the eye orbit (e.g. eye socket). The cavity 112 can include a spatial volume, such as the spatial volume defined between an inner surface 188 of the cover 110 and an anterior surface of the patient eye. The cavity 112 can contain a working fluid, such as a liquid or gaseous fluid, that can form an eye environment in contact with the patient eye. In an example, the eye environment can be used to characterize a physiological state of the patient eye, such as the eye environment can include physiological constituents including biomarkers emitted from the eye. Information sensed by the apparatus 100, such as biomarkers sensed from the working fluid in the cavity 112, can provide a medical professional with patient information, such as to diagnosis an eye condition associated with the patient eye. In an example, the eye environment can be used to treat a patient eye, such as the apparatus 100 can adjust the eye environment to vary at least one of pressure in the cavity 112 or the working fluid composition to treat an eye condition.

An eye condition can describe a state of an eye, such as a physiological state of the eye that can affect the vision of a patient. An eye condition can include at least one of an acute eye condition, such as an eye condition that can persist for a period of time measured in seconds, minutes, or days, or a chronic eye condition, such as an eye condition that can persist for a period of time measured in days, weeks, months, or years. In an example, an eye condition can include an abnormal eye condition, such as an eye experiencing a disease state. A disease state of the eye can include at least one of glaucoma, papilledema, such as optic disk edema, Fuchs dystrophy, diabetic retinopathy, macular degeneration, such as wet or dry macular degeneration, cataract, dry eye, corneal infection, meibomian gland disease, demodex, corneal ectasia, or periocular skin laxity.

The eye condition can be affected by the apparatus 100, such as by exposing the patient eye, including the anterior portion of the eye, to the eye environment in the cavity 112. In an example, glaucoma can be treated, inhibited, or prevented with the apparatus 100, such as by exposing the eye to an eye environment including a negative gauge pressure. In an example, optic disk edema can be treated, inhibited, or prevented with the apparatus 100, such as by exposing the eye to an eye environment including a positive gauge pressure. In an example, an aerobic eye infection can be treated, inhibited, or prevented with the apparatus 100, such as by exposing the eye to an anerobic environment (e.g., an environment without oxygen), such as to address the underlying cause of the aerobic eye infection.

One or more eye conditions can be affected by the apparatus 100, such as simultaneously affected, by exposing the eye to the environment in the cavity 112. In an example, where a patient can experience one or more eye conditions, such as glaucoma and an aerobic eye infection, the eye conditions can be treated, inhibited, or prevented with the apparatus 100, such as by exposing the patient eye to an eye environment including a negative gauge pressure anerobic eye environment, such as the negative pressure environment to treat glaucoma and the anerobic environment to treat the aerobic eye infection.

The eye environment can be defined by an environmental parameter, such as a characteristic of the working fluid in the cavity 112. An environmental parameter can include at least one of working fluid flow in the cavity 112, such as working fluid volumetric flow rate into or out of the cavity 112, working fluid humidity in the cavity 112, such as the relative humidity of the working fluid in the cavity 112, working fluid temperature in the cavity 112, working fluid pressure in the cavity 112 (e.g., cavity pressure), such as the working fluid gauge pressure in the cavity 112 and the ambient pressure of the environment surrounding the cavity, or working fluid composition in the cavity 112, such as working fluid composition measured by at least one of constituent fluid concentration or partial fluid pressure.

Exposure of the eye to the eye environment can cause a change in the eye, such as absorption of the working fluid into the eye can cause a change in a physiological parameter associated with the eye. A physiological parameter can include at least one of intraocular pressure (IOP), intracranial pressure (ICP), such as cerebrospinal fluid pressure (CSFP), or spontaneous venous pulsation (SVP), such as an SVP state.

The cover 110 can retain the working fluid against the patient, such as in contact with the anterior portion of the patient eye, to form an eye environment in the cavity 112. Exposure of the patient eye to the eye environment can affect a treatment of the eye, such as at least one of a diagnostic test of the eye or a therapeutic treatment of the eye, such as to treat, inhibit or prevent an eye condition associated with the eye. Treatment of the eye can include exposure of the eye to at least one of the working fluid pressure in the cavity 112, such as to apply a force to the anterior portion of the eye to adjust intraocular pressure (IOP) level in the eye, or exposure of the eye to the working fluid composition in the cavity 112, such as to facilitate absorption of the working fluid into the eye including through the anterior portion of the eye.

The cover 110 can maintain a differential fluid pressure, such as a gauge pressure of the working fluid in the cavity 112, in contact with the patient eye. In an example, gauge pressure can be defined as the difference in pressure between the working fluid pressure in the cavity 112 and atmospheric pressure surrounding the cover 110. A positive gauge pressure, such as where working fluid pressure in the cavity 112 is greater than atmospheric pressure, can create a compressive working fluid force on the anterior surface of the eye, such as to increase intraocular pressure (IOP) in the eye. A negative gauge pressure, such as where working fluid pressure in the cavity 112 is less than atmospheric pressure, can create a negative (or "vacuum") working fluid force on the anterior surface of the eye, such as to decrease TOP in the eye. In at least one example, the working fluid in the cavity 112 can include a readily compressible fluid, such as a gaseous fluid with the same composition as ambient air.

The working fluid force applied to the anterior surface of the eye can include a perturbation force, such as a force for a diagnostic test. The perturbation force can be applied to the anterior surface of the eye for a period of time sufficient to allow for measurement of the deflection of the eye, such as deflection from a first position to a second position. In an example, application of a perturbation force for a period measured in seconds or minutes can be sufficient for deflection measurement. The perturbation force can be generated by a positive gauge pressure in the cavity 112 to exert a positive perturbation force on the eye, such as to decrease the curvature of the eye for a diagnostic test including a diagnostic measurement. The perturbation force can be generated by a negative gauge pressure in the cavity 112 to exert a negative perturbation force on the eye, such as to increase the curvature of the eye for a diagnostic test including a diagnostic measurement.

The force applied to the anterior surface of the eye can include a therapeutic force, such as a force to apply a therapy regimen to the anterior surface of the eye for a period of time sufficient to treat an eye condition including an acute eye condition or a chronic eye condition. In an example, application of a therapeutic force for a period measured in days, weeks, months, or years can be applied depending on the eye condition treated. The therapeutic force can be generated by a positive gauge pressure to exert a positive therapeutic compressive force on the eye, such as to increase the intraocular pressure (or TOP) of the eye to inhibit, treat, or prevent an eye condition including optic disc edema. The therapeutic force can be generated by a negative gauge pressure that can exert a negative therapeutic force on the eye, such as to decrease the TOP of the eye to inhibit, treat, or prevent an eye condition including glaucoma.

An eye condition can include at least one of an acute eye condition, such as an eye condition that can persist for a duration measured in seconds, minutes, or days, or a chronic eye condition, such as an eye condition that can persist for a duration measured in days, weeks, months, or years. In at least one example, an eye condition can include at least one of glaucoma, edema, such as optic disk edema, Fuchs dystrophy, diabetic retinopathy, macular degeneration, such as wet or dry macular degeneration, cataract, dry eye, corneal infection, memobian (meibomian) gland disease, demodex, corneal ectasia, or periocular skin laxity.

The working fluid can be composed of one or more constituent fluids, such as a combination of one or more liquids or gases. A working fluid can include a combination of two constituent fluids, such as a combination of gaseous nitric oxide and gaseous carbon dioxide. A constituent fluid can include a therapeutic fluid, such as a component of the constituent fluid can be absorbed through the eye to inhibit, treat, or prevent an eye condition. For example, a working fluid can include a combination of nitrogen and nitric oxide, such as the nitric oxide constituent can be absorbed through a surface of the eye to promote vasodilation of blood vessels in the eye to treat an eye condition including glaucoma.

A therapeutic fluid can include a gaseous therapeutic fluid, such as carbon dioxide ($CO_2$), oxygen ($O_2$), nitric oxide (NO), ozone ($O_3$), nitrogen ($N_2$), helium (He), hydrocarbons including fluorocarbons and perfluorocarbons, sulfur hexafluoride, cannabinoids including tetrahydrocannabinol (THC) and cannabidiol (CBD), a combination of two or more gaseous therapeutic fluids, or the like. In an example, a therapeutic gas can include a mixture of at least one of carbon dioxide, oxygen, or nitric oxide, such as to treat an eye condition. In an example, a therapeutic gas can include a mixture of nitric oxide and oxygen including a mixture of 50% nitric oxide and 50% oxygen, a mixture of helium and oxygen (also known as heliox), and Medical Air including Medical Grade Air USP, such as to treat an eye condition. In an example, a mixture of therapeutic gases can include a mixture of nitric oxide and oxygen, such as a mixture of 50% nitric oxide and 50% oxygen including gases from The BOC Group plc under the tradename ENTONOX, such as to treat an eye condition. In an example, a combination of therapeutic gases can include a mixture of helium and oxygen, such as a mixture of 21% oxygen and 79% helium, also known as heliox, such as to treat an eye condition. In an example, a combination of therapeutic gases can include a mixture of at least one of fluorine or chlorine, such as to treat an eye condition including an eye infection. In an example, a combination of therapeutic gases can include at least one of a mixture with a volume fraction of oxygen less than ambient air, such as the mixture with less than about twenty-one percent volume fraction $O_2$, such as to treat an aerobic eye infection, or a mixture with a volume fraction of oxygen greater than ambient air, such as the mixture with more than about twenty-one percent volume fraction $O_2$, such as to treat an anaerobic eye infection.

A therapeutic fluid can include a liquid therapeutic fluid, such as a therapeutic solution. The therapeutic solution can include a solvent, such as water ($H_2O$), and a solute, such as a therapeutic solute. The therapeutic solute can include at least one of vitamin A, B vitamins, such as riboflavin (vitamin B2), Vitamin C, Vitamin D, Vitamin E, beta-carotene, zinc, lutein, or folate. The therapeutic solution can be converted from a liquid therapeutic fluid to a gaseous therapeutic fluid, such as with a nebulizer or an atomizer to form a therapeutic mist or fog, for delivery to the cavity 112 and contact with the patient eye. In an example, a patient eye can be exposed to a gaseous therapeutic fluid, such as a therapeutic mist including Vitamin A, to achieve a first therapeutic result, such as treatment of a corneal ulcer. In an example, a patient eye can be exposed to a gaseous therapeutic fluid, such as a therapeutic mist including riboflavin, and subsequently exposed to potentiating energy, such as ultraviolet light, to achieve a second therapeutic result, such as increased corneal cross-linking to treat keratoconus.

The cover 110 can include a first port 114. The first post 114 can be located in a surface of the cover 110, such as the first port 114 can extend from an outer surface 187 of the cover 110 to an inner surface 188 of the cover 110, to allow access to the eye environment in the cavity 112. The first port 114 can include a septum, such as a flexible septum located over the first port 114 to isolate the cavity 112 from the surrounding environment. The flexible septum can maintain a gauge pressure, such as at least one of a positive or negative gauge pressure, in the cavity 112.

The flexible septum can include a resealable septum, such as a septum formed from a self-healing material including a self-sealing polymer material that can allow the insertion and withdrawal of instruments through the septum into the cavity 112 while maintaining a gauge pressure in the cavity 112. In an example, the resealable septum can allow a hypodermic needle to be inserted and withdrawn through the resealable septum while maintaining a gauge pressure (e.g. a positive or negative gauge pressure) in the cavity 112. For example, the resealable septum can allow for a hypodermic needle to be placed in proximity of the eye, such as to place a therapeutic fluid in contact with the eye, while maintaining a gauge pressure in the cavity 112.

The flexible septum can include a measurement septum, such as a septum to allow a sensor, such as the sensor 130, to sense an indication of the eye environment in the cavity 112 without contacting the eye environment. In an example, a pressure sensor can be located in contact with the measurement septum covering the first port 114 of the cover 110, such as to sense an indication of working fluid pressure in the cavity 112 through the pressure measurement septum.

The cover 110 can include a second port 116, extending from an outer surface 187 of the cover 110 to an inner surface 188 of the cover 110. In an example, the second port 116 can place the cavity 112 in communication with the pressure source 150, such as with a conduit 117.

The cover 110 can include a seal 119, such as to provide an interface including a cover-patient interface between the cover 110 and the patient to improve patient comfort when wearing the apparatus 100. The seal can also serve as a barrier, such as to separate the eye environment in the cavity 112 from the surrounding environment. The seal 119 can attach to the periphery of the cover 110, such as at least a portion of the periphery of the cover 110. In an example, the seal 119 can extend continuously around the periphery of the cover, such as to form a sealing surface between the cover 110 and the patient 119 to separate the volume of the cavity 112 from the surrounding environment.

The apparatus 100 can include a cavity check valve 189. The cavity check valve 189 can be located on the apparatus 100 in communication with the cavity 112, such as on at least one of the cover 110 including any surface of the cover 110, the conduit 117, the control circuitry 140, or the pressure source 150. In an example, the cavity check valve 189 can be located in proximity to, such as in, on, or over, the first port 114.

The cavity check valve 189 can limit the working fluid pressure applied to the cavity 112. In an example, the cavity check valve 189 can be used as a safety valve, such as to ensure that pressure in the cavity 112 will not exceed cavity pressure levels that could damage the eye. In an example, the cavity check valve 189 can limit pressure in the cavity 112 to a target cavity pressure level.

The cavity check valve 189 can include a cracking pressure, such as a characteristic of the cavity check valve 189 that can control initiation of fluid flow through the valve. In an example, the cracking pressure can describe an inlet pressure level of the cavity check valve 189 at which a fluid can initiate flow through the cavity check valve 189. Working fluid pressure in the cavity 112 can be limited to the target cavity pressure level by selecting or setting the cracking pressure of the cavity check valve 189, such as by selecting or setting the cracking pressure of the cavity check valve 189 to equal the target cavity pressure level. For example, when the working fluid pressure in the cavity 112 is less than the cracking pressure of the cavity check valve 189, the cavity check valve 189 can assume a closed state, such as to prevent the flow of working fluid from the cavity to the surrounding atmosphere. When the working fluid pressure in the cavity 112 is equal to or greater than the cracking pressure of the cavity check valve 189, the cavity check valve 189 can assume an open state, such as to allow the flow of working fluid from the cavity 112 to the surrounding atmosphere.

The cavity check valve 189 can include a passive cavity check valve, such as a flapper valve or a poppet valve. The cracking pressure of the passive cavity check valve can be adjusted, such as by changing the dimensions of the passive cavity check valve or components of the passive cavity check valve. In an example, the cracking pressure of a flapper cavity check valve can be adjusted, such as by changing at least one of the flapper check valve dimensions (e.g., length, width, thickness), the flapper check valve constituent material (e.g. type of material, durometer of material, single or multi-ply material, stiffness of valve), or the flapper check valve hinge. In an example, the cracking pressure of a poppet cavity check valve can be adjusted, such as by changing at least one of the poppet valve dimensions (e.g., spring stiffness, poppet diameter).

Figure 2A:
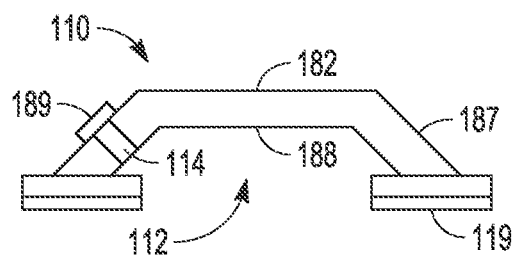
FIG. 2A shows a side view of an example positive pressure cavity check valve in an open position.
Figure 2B:
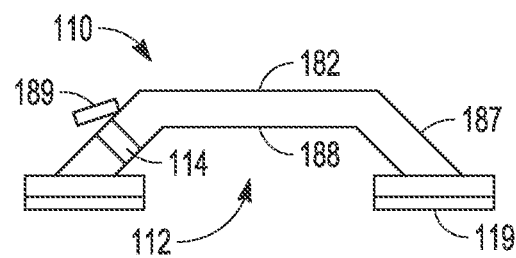
FIG. 2B shows a side view of an example positive pressure cavity check valve in a closed position.

FIGS. 2A and 2B show a side view of an example of a positive pressure cavity check valve, such as a flapper valve configured to control pressure in the cavity 112 to a positive target cavity pressure level. The positive target cavity pressure level can be specified, such as by a medical professional to treat, inhibit, or prevent an eye condition. The positive pressure cavity check valve can be located on the cover 110, such as the outer surface 187 of the cover 110 to allow positive pressure working fluid in the cavity 112 at a pressure greater than the cracking pressure of the check valve to flow from the cavity 112 to the surrounding environment.

As shown in FIG. 2A, the cavity check valve 189 can assume a closed position, such as working fluid cannot pass from the cavity 112 through the cavity check valve 189 to the surrounding environment. In the closed position, the apparatus 100 can support a positive gauge pressure environment in the cavity 112, such as a positive gauge pressure level less than the positive target cavity pressure level. The positive target cavity pressure level can be controlled, such as by setting the cracking pressure of the positive pressure cavity check valve to equal the positive target cavity pressure level.

As shown in FIG. 2B, the cavity check valve 189 can assume an open position, such as working fluid can pass from the cavity 112 through the cavity check valve 189 to the surrounding environment, such as when the positive gauge pressure in the cavity 112 is equal to or greater than the positive target cavity pressure level. In the open position, the apparatus 100 can limit the positive gauge pressure environment in the cavity 112 to a pressure level approximately equal to the positive target cavity pressure level, such as to protect the eye from excessive working fluid pressure.

Figure 3A:
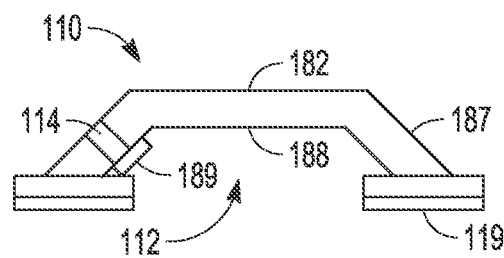
FIG. 3A shows a side view of an example negative pressure cavity check valve in a closed position.
Figure 3B:
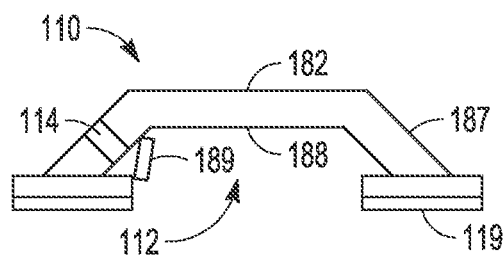
FIG. 3B shows a side view of an example negative pressure cavity check valve in an open position.

FIGS. 3A and 3B show a side view of an example of a negative pressure cavity check valve, such as a flapper valve configured to control pressure in the cavity 112 to a negative target cavity pressure level. The negative target cavity pressure level can be specified, such as by a medical professional to treat, inhibit, or prevent an eye condition. The negative pressure cavity check valve can be located on the cover 110, such as the inner surface 188 of the cover 110 to allow fluid from the surrounding environment to flow into the cavity 112 from the surrounding environment.

As shown in FIG. 3A, the cavity check valve 189 can assume a closed position, such as ambient fluid cannot pass into the cavity 112 through the cavity check valve 189 from the surrounding environment. In the closed position, the apparatus 110 can support a negative gauge pressure environment in the cavity 112, such as a negative gauge pressure level greater than the negative target cavity pressure level. The negative target cavity pressure level can be controlled, such as by setting the cracking pressure of the negative pressure cavity check valve to equal the negative target cavity pressure level.

As shown in FIG. 3B, the cavity check valve 189 can assume an open position, such as ambient fluid can pass into the cavity 112 through the cavity check valve 189 from the surrounding environment, such as when the negative gauge pressure in the cavity 112 is equal to or less than the negative target cavity pressure level. In the open position, the apparatus 100 can limit the negative gauge pressure environment in the cavity 112 to a pressure level approximately equal to the negative target cavity pressure level, such as to prevent possible damage to the eye by excessive working fluid pressure.

As the patient eye condition changes, such as improves or degrades, a medical professional can adjust the prescribed treatment regimen, such as to change at least one of the positive target cavity pressure level or the negative target cavity pressure level. To adjust a target pressure level, the assembly 100 can include an adjustable valve. In an example, an adjustable valve can include a replaceable valve, such as a replaceable check valve assembly.

Figure 4:
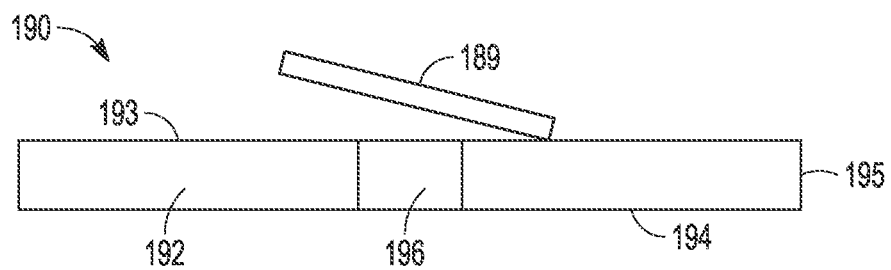
FIG. 4 shows a side view of an example check valve assembly.

FIG. 4 shows a side view of an example of a check valve assembly 190, such as a flapper check valve assembly in an open position. The apparatus 100 can include a check valve assembly 190, such as a replaceable check valve assembly 190 to adjust the target cavity pressure level in the cavity 112. In an example, the apparatus 100 with a first check valve assembly including a first cavity check valve with a first cracking pressure set to a first target pressure level, can be replaced with a second check valve assembly including a second cavity check valve with a second cracking pressure set to a second target pressure level, such as to realize a change in pressure applied to an eye specified in a prescribed patient treatment regimen including a change in target cavity pressure level.

The cavity check valve assembly 190 can include a base 192 with a first side 193, a second side 194 parallel to the first side 193, a base periphery 195 extending from the first side 193 to the second side 194, a base port 196 extending through the base 192 from the first side 193 to the second side 194, and a cavity check valve 189 located on the first side 193 over the base port 196, such as at least a portion of the base port 196. The cavity check valve assembly 190 can be located in the apparatus 100, such as in the cover 110 so that the base periphery 195 can be in contact with the cover 110, such as at least a portion of the surface of the port 114.

The check valve assembly 190 can be located on the apparatus 100 in communication with the cavity 112, such as on at least one of the cover 110 including any surface of the cover 110, the conduit 117, the control circuitry 140, or the pressure source 150. The cavity check valve assembly 190 can be located in contact with the cover 110, such as the base periphery 195 can be in contact with at least a portion of the cover 110, such as at least one of the surface of the port 114, the outer surface 187, or the inner surface 188. The cavity check valve assembly 190, such as a positive pressure check valve assembly, can be configured to control pressure in the cavity 112 to a positive target cavity pressure level, such as the check valve assembly 190 can be located in the port 114 so that the cavity check valve 189 can be located outside of the cavity 112. The cavity check valve assembly 190, such as a negative pressure check valve assembly, can be configured to control pressure in the cavity 112 to a negative target cavity pressure level, such as the check valve assembly 190 can be located in the port 114 so that the cavity check valve 189 can be located inside the cavity 112.

Referring again to FIG. 1, the fluid regulator 120 can regulate the flow of fluid between two reservoirs, such as the fluid flow between the cavity 112 and a fluid source 170, such as a pressurized gas cylinder. The fluid regulator 120 can include a regulator valve, such as to regulate flow rates between the first and second reservoirs. The regulator valve can include a passive valve, such as a check valve that closes as pressure exceeds a critical value. In an example, a fluid regulator 120 with a check valve can be located between the cover 110 and a fluid source 170, such as if the pressure of the fluid source 170 exceeds a critical value, such as a pressure that can cause damage to a patient eye, the check valve can close to isolate pressure of the fluid source 170 from the patient eye, such as to protect the patient eye from excessive force. The regulator valve can include an active valve, such as an electrically-modulated valve including a servo valve, or a proportional valve, such as a piezo-actuated proportional valve. In an example, the regulator valve can receive a control signal, such as from the control circuitry 140, to modulate the position of the electrically-modulated spool with respect to the valve body, such as to regulate fluid flow through the electrically-modulated valve.

The fluid regulator 120 can attach to a fluid source 170, such as to regulate the flow of fluid from the fluid source 170 to the cavity 112. The fluid source 170 can include a fluid vessel, such as a storage container of pressurized gaseous fluid. The fluid source 170 can include a generator device, such as a device that concentrates or distills a constituent fluid from another fluid. In an example, a generator device can include a concentrator, such as an oxygen concentrator or a carbon dioxide concentrator. In an example, a generator device can include an atomizer, such as an ultrasonic humidifier or an aerosolizer, to transform a liquid therapeutic fluid, such as a miscible solution or colloidal suspension, into a gaseous working fluid, such as a therapeutic mist or fog.

The fluid regulator 120 can communicate with apparatus 100, such as the fluid regulator 120 can communicate with the cavity 112. In an example, the fluid regulator 120 can be connected to the cover 110, such as with the conduit 117 in direct communication with the cover 110 through the second port 116. In an example, the fluid regulator 120 can be connected to the conduit 117 in communication with the cover 110 by a tube connector 118, such as a Y-connector. In an example, the fluid regulator 120 can be connected to the control circuitry 140, such as to receive a control signal from the control circuitry 140 to adjust the position of a servo valve.

The sensor 130 can sense an indication of the eye environment in the cavity 112, such as at least one of an indication of a characteristic of the working fluid in the cavity 112 or an indication of a physiological parameter of the patient. The sensor 130 can include sensor circuitry, such as sensor circuitry to receive an indication of a physical parameter sensed by the sensor 130 and process the received indication, such as into an indication including an electrical signal suitable to be received by at least one of the control circuitry 140 or the pressure source 150.

The sensor 130 can be located in proximity to the apparatus 100, such as in communication with the cavity 112 or at least partially attached to the patient. In an example, the sensor 130 can be separate from the apparatus 100. For example, the sensor 130 can include a handheld pressure gauge, such as to be pressed against a measurement septum located over the port 114 to sense an indication of working fluid pressure in the cavity 112. In an example, the sensor 130 can be in fluidic communication with the cavity 112, such as the sensor 130 can be located in the cavity 112 or on the control circuitry 140 in fluidic communication with the cavity 112. In an example, the sensor 130 can be at least partially attached to the patient, such as to a surface of the eye including an anterior surface of the eye or patient tissue covering the skull including tissue over the frontal, parietal, sphenoid, temporal, zygomatic, maxillary, occipital, and mandibular bones. For example, the sensor 130 can include an electroretinography device, such as part of which can include an electrode attached to patient tissue to sense an indication of electrical activity in the patient including electrical activity associated with a pattern electroretinography (or PERG) test. The sensor 130 can be in electrical communication with the apparatus, such as at least one of the control circuitry 140 or the pressure source 150. The sensor 130 can provide at least one of continuous or periodic (e.g. intermittent) sensing of the working fluid, such as for monitoring an indication of the eye environment with the sensor 130, or an indication of the physiological parameter associated with the patient, such as IOP or CSFP.

The sensor 130 can include an TOP sensor, such as a device to sense an indication of an intraocular pressure (IOP) level in the eye. The TOP sensor can include at least one of an invasive IOP sensor, such as an IOP sensor implantable in an intraocular space of the eye to sense IOP including a sensor from Implandata Ophthalmic Products GmbH (Hannover, Germany) offered for sale under the trademark EYEMATE® or a non-invasive IOP sensor, such as an IOP sensor to sense IOP without implantation into the body including a contact lens-based sensor from Sensimed AG (Lausanne, Switzerland) offered for sale under the trademark SENSIMED TRIGGERFISH®.

The IOP sensor can include at least one of a continuous IOP sensor, such as an IOP sensor capable of continuous sensing of IOP level in the patient eye, or a periodic IOP sensor, such as an IOP sensor that capable of sensing IOP level in the patient eye at periodic or aperiodic intervals. In an example, the periodic IOP sensor can include a tonometer, such as a handheld tonometer designed for patient self-monitoring of IOP. The data sensed by the IOP sensor can be received by the control circuitry 140, such as to facilitate use of the apparatus 100.

The sensor 130 can include a cardiac sensor, such as to detect an indication of cardiac activity in a patient. An indication of cardiac activity can include at least one of an indication of systemic blood pressure, such as an indication of systolic and an indication of diastolic blood pressure, or an indication of heart rate.

The cardiac sensor can include a blood pressure (BP) sensor, such as a device to sense an indication of blood pressure level including systemic blood pressure level, in the patient. The BP sensor can include at least one of an invasive BP sensor, such as a BP sensor implantable within the patient, and a non-invasive BP sensor, such as a BP sensor that can sense BP without implantation within the patient body.

The sensor 130 can include a working fluid flow sensor, such as a device to sense an indication of working fluid flow including at least one of volumetric flow rate or mass flow rate into or out of the cavity 112. The sensor 130 can include a humidity sensor, such as a device to sense an indication of the relative humidity of the working fluid in the cavity 112. The sensor 130 can include a thermometer, such as a device to sense an indication of the temperature of the working fluid in the cavity 112. The sensor 130 can include a displacement sensor, such as a device to sense an indication of displacement including an optical coherence tomography device configured to sense displacement of structures associated with the patient eye.

The sensor 130 can include a pressure sensor, such as a device to sense an indication of working fluid pressure in the cavity 112. The pressure sensor can be located in proximity to the cavity 112, such as in communication with the cavity 112. In an example, the pressure sensor can include a cavity pressure sensor, such as a pressure sensor located in the cavity 112.

In an example, in some cases, working fluid pressure in the cavity 112 can serve as an estimate (e.g., an approximation) for intraocular pressure (IOP) in the eye. However, due to characteristics of the eye, such as corneal thickness and cornea rigidity, cavity pressure may not serve as a surrogate of IOP in the eye.

Static cavity pressure level in the cavity 112, such as the pressure level sensed by the pressure sensor when the pressure source 150 is not adjusting working fluid pressure in the cavity 112, can be the same at any location in the cavity 112. Dynamic cavity pressure level, such as the pressure level sensed by the pressure sensor when the pressure source 150 is adjusting working fluid pressure in the cavity 112, can vary depending on the location of the pressure sensor in communication with the cavity 112.

The sensor 130 can include a pressure sensor in combination with another indication, such as an indication of the operating state of the pressure source 150, to estimate a static cavity pressure level in the cavity 112. In an example, the pressure sensor, such as a pressure-flow sensor including a sensor that can measure both working fluid pressure (static and dynamic) and working fluid flow at a measurement location, can be located in proximity to the pressure source 150, such as an inlet port or an outlet port of the pressure source 150, to sense an indication of dynamic pressure at the pressure sensor location and include circuitry, such as sensor circuitry to receive an indication of the operation state of the pressure source 150 including an indication of flow rate (e.g., pump speed can be proportional to flow rate). The pressure-flow sensor can process at least one of the indication of dynamic pressure or the indication of flow rate, such as to form a control signal that can be received by the pressure source 150 to achieve a static cavity pressure level, such as a target pressure level, in the cavity 112. The control signal can be based on a relationship between the indication of dynamic pressure and the indication flow rate, such as a relationship between pressure and flow including the relationship described by a p-Q (e.g., pressure-flow) chart that can account for the operating characteristics of the pressure source 150.

In an example, the pressure sensor can be located in proximity to the pressure source 150. The control circuitry 140 can be configured to receive an indication of dynamic pressure from the pressure sensor and an indication of the operation state of the pressure source 150 including an indication of pump speed. The control circuitry 140 can process at least one of the indication of dynamic pressure or the indication of pressure source 150 operation state, such as to form a control signal that can be received by the pressure source 150 to achieve a static cavity pressure level, such as a target pressure level, in the cavity 112.

The sensor 130 can include a concentration sensor or a working fluid composition sensor, such as a device to sense an indication of a chemical constituent in the working fluid. In an example, the concentration sensor can be configured to sense an indication of the working fluid, such as a constituent in the working fluid. The constituent in the working fluid, such as the constituent in the working fluid delivered to the cavity 112, can include a therapeutic fluid. In at least one example, the working fluid composition sensor can sense a therapeutic fluid, such as at least one of ($CO_2$), oxygen ($O_2$), nitric oxide (NO), ozone ($O_3$), nitrogen, helium (He), hydrocarbons including fluorocarbons and perfluorocarbons, sulfur hexafluoride, cannabinoids including tetrahydrocannabinol (THC) and cannabidiol (CBD), or a combination of therapeutic gases.

The sensor 130 can include a biomarker sensor, such as a device to sense an indication of a biomarker including a chemical constituent. A chemical constituent in the working fluid can include a biomarker, such as a biomarker emitted by the patient eye or sensed within the patient eye. A biomarker can suggest a physiological state of the eye, such as a state of distress where medical intervention can be required. The biomarker sensor can include a ketone, such as can be detected with a volatile gas sensor including a quartz crystal nanobalance (QCN) sensor, glucose, such as can be detected with an optical glucose sensor including an OCT imaging system, oxygen levels, such as can be detected with a non-invasive optical oxygen sensor, dissolved salts, such as can be detected with a salinity sensor, and vascular endothelial growth factor (or VEGF), such as can be detected with an aptamer-based sensor including the sensor and methods described in the publication "Flexible FET-Type VEGF Aptasensor Based on Nitrogen-Doped Graphene Converted from Conducting Polymer", by Kwon, et at., ACS Nano, Vol. 6, #2, pages 1486-1493, published February 2012, and incorporated herein by reference in its entirety. A biomarker can include at least one of an enzyme, such as matrix metallopeptidase 9 (MPP-9), that can be detected with an enzyme sensor or a protein, such as brain-derived neurotrophic factor (BDNF), that can be detected with a protein sensor.

The sensor 130 can include a biosensor, such as a sensor configured to sense an indication of a physiological parameter associated with a patient. A physiological parameter can include an indication of a physiological process associated with the patient, such as a process associated with a patient eye or process associated with physiological activity of the patient eye. In an example, a physiological parameter can include at least one of an indication of intraocular pressure (IOP) in the patient eye, such as an IOP level, an indication of cerebrospinal fluid pressure (CSFP) associated with the patient, such as a CSFP level, an indication of cardiac activity, such as at least one of systemic blood pressure or heart rate. A physiological parameter can include an indication of retinal activity, such as measured by an electroretinography device including a pattern electroretinography (or PERG) device.

The sensor 130 can include an imaging sensor to sense an indication of the eye, such as an intraocular portion of the eye. The imaging sensor can be located in proximity to the eye, such as attached to apparatus 100 including the cover 110 or exist separately from the apparatus including as a stand-alone device. In an example, the imaging sensor can include a camera, such as a single image capture camera or a multi-image capture camera including a video camera, such as the one or more captured images can be transferred to the apparatus 100 for image processing. In an example, the imaging sensor can include an optical coherence tomography (OCT) device.

The sensor 130 can include a blood flow sensor, such as an ocular blood flow sensor. The blood flow sensor can include an invasive blood flow sensor ocular imaging system, such as a blood flow sensor an imaging system that requires at least a part component of the system to be inserted into the patient. In an example, an invasive blood flow sensor an invasive ocular imaging system can include a fluorescein angiography system.

The blood flow sensor can include a non-invasive ocular blood flow sensor ocular imaging system, such as an ocular blood flow sensor an imaging system that does not require a component of the sensor imaging system to be inserted into the patient. The non-invasive ocular blood flow sensor ocular imaging system can include a system to sense an indication of ocular blood flow from a patient or circuitry to process information from the patient to yield an indication of ocular blood flow. An indication of ocular blood flow can include at least one of peak systolic blood velocity (PSV), end diastolic blood velocity (EDV), mean blood velocity (MV), resistivity index (RI), such as RI=(PSV−EDV)/PSV, or pulsatility index (PI), such as PI=(PSV−EDV)/MV.

The non-invasive ocular blood flow sensor ocular imaging system can include an ocular energy source, such as to radiate illuminate a tissue including ocular tissue with energy to elicit a response from the tissue that can be sensed with a sensor. The ocular tissue can be illuminated with electromagnetic (EM) energy generated by the ocular energy source, such as EM energy in a frequency range from about 3 hertz (Hz) to about 300 exahertz (EHz). In an example, an ocular energy source can include a diffuse light source, such as generated by a light bulb, and a collimated light source, such as generated by a laser diode.

The non-invasive ocular blood flow sensor ocular imaging system can include an ocular blood flow sensor, such as to sense energy radiated from ocular tissue including energy elicited from the ocular tissue by illuminating the ocular tissue with an energy source. An ocular blood flow sensor can be configured to sense EM energy, such as EM energy in a frequency range from about 3 hertz (Hz) to about 300 exahertz (EHz).

In an example, the ocular blood flow sensor can include an ultrasonic sensor, such as an ultrasonic sensor configured to sense EM energy in a frequency range from about 3 Hz to about 300 gigahertz (GHz) including a frequency range from about 20 kilohertz (kHz) to about 400 kHz and a frequency range of about 1 megahertz (MHz) to about 18 MHz.

The ocular blood flow sensor can include a charge coupled device (CCD) sensor including a complementary metal-oxide-semiconductor (CMOS) sensor. The CCD sensor can be configured to sense EM energy in a frequency range from about 300 GHz to about 300 EHz including a frequency range from about 300 GHz to about 400 tetrahertz or THz (infrared radiation, corresponding to wavelengths of about 1,000 micrometers to about 750 nanometers or nm), a frequency range from about 400 THz to about 800 THz (visible light, corresponding to wavelengths of about 750 nm to about 375 nm), and a frequency range from about 800 THz to about 30 petahertz or PHZ (ultraviolet radiation, corresponding to wavelengths of about 375 nm to about 10 nm).

The non-invasive ocular blood flow sensor ocular imaging system can include a color doppler imaging (CDI) system, such as a medical ultrasonic imaging system with at least one of an ocular energy source, such as an ultrasonic transducer, an ocular blood flow sensor, such as an ultrasonic receiver, or a combination of ocular energy source and ocular blood flow sensor, such as an ultrasonic transceiver. In an example, the CDI system can be configured with an energy source capable of generating EM energy at a frequency of about 6.5 MHz.

The non-invasive ocular blood flow sensor system ocular imaging can include a laser speckle flowgraphy (LSF) or laser speckle contrast imaging (LSCI) system. In an example, the LSF system can be configured with an energy source capable of generating EM energy at a frequency of about 361 THz (corresponding to a wavelength of about 830 nm). In an example, the LSF system can include a system from Nidek Co., Ltd. (Aichi, Japan) offered for sale under the tradename LSFG-Retflow.

The non-invasive ocular blood flow sensor system can include a laser Doppler flowmeter (LDF), such as a confocal scanning laser Doppler flowmetry (CSLDF) system. In an example, the LDF system can be configured with an energy source capable of generating EM energy at a frequency of about 384 THz (corresponding to a wavelength of about 780 nm). In an example, the CSLDF system can include a system from Heidelberg Engineering GmbH (Heidelberg, Germany) offered for sale under the tradename Heidelberg Retina Flowmeter.

The non-invasive ocular blood flow sensor system can include an ocular coherence tomography angiography (OCTA) system. In an example, the function of an ocular coherence tomography (OCT) system can be enhanced, such as by placing an OCTA module in communication with the OCT system. An OCTA module can include control circuitry that can execute coded instructions to cause the OCT system to repeatedly scan a section of eye tissue, store each scan of eye tissue into memory, and process the stored scans to identify differences between scans, such as to generate an indication of ocular blood flow. In an example, the OCTA system can include at least one of an OCT system from Heidelberg Engineering GmbH (Heidelberg, Germany) offered for sale under the tradename Spectralis or an OCTA module from Heidelberg Engineering GmbH (Heidelberg, Germany) offered for sale under the tradename Spectralis OCT Angiography Module.

The non-invasive ocular blood flow sensor system can include a laser doppler velocimetry (LDV) system. In an example, the LDV system can be configured with an energy source capable of generating EM energy at a frequency of about 444 THz (corresponding to a wavelength of about 675 nm).

The non-invasive ocular blood flow sensor system can include a retinal vessel analyzer (RVA) system. The RVA system can include a system that illuminates the eye vessel and senses at least one of a coefficient of light reflection or a coefficient of light absorption.

The non-invasive ocular blood flow sensor system can include a doppler optical coherence tomography (DOCT) system with a collimated light source, such as a collimated light source configured to illuminate ocular tissue and a CCD sensor configured to receive the collimated light reflected from the ocular tissue. In an example, the DOCT system can be configured with an energy source capable of generating EM energy at a frequency of about 356 THz (corresponding to a wavelength of about 841 nm). In an example, the DOCT system can include the DOCT system from Optovue, Inc (Fremont, Calif.) offered for sale under the tradename RTVue.

The non-invasive ocular blood flow sensor system can include at least one of a retinal functional imager (RFI) system, a pulsatile ocular blood flow (POBF) system, a fundus pulsation amplitude (FPA) system, a fluorescein and Indocyanine Angiography (FA, ICG) system, a color doppler imaging (CDI) system, a retinal oximetry system, a magnetic resonance imaging (MRI) system, a magnetic resonance imaging (MRI) system, a blue light entoptoscopy) system, a frequency domain optical coherence tomography (FD-OCT) system, an angiography system, or a Split Spectrum Amplitude Decorrelation Angiography with Optical Coherence Tomography (SSADA-OCT) system.

The non-invasive ocular imaging system can include an electroretinography (ERG) system, such as at least one of a full field, multifocal, pattern, or visual evoked potential (VEP) electroretinography system. In an example, the ERG system can be configured with an energy source capable of generating EM energy at a frequency of about 440 THz (corresponding to a wavelength of about 680 nm or greater). In an example, the ERG system can include a system from Diopsys, Inc. (Pine Brook, N.J.) offered for sale under the tradename Diopsys Nova-ERG.

The ERG system can include a recording electrode, such as to sense an indication of electrical activity in the eye, including at least one of a neural and a non-neuronal cell in the retina, from stimulus applied to the eye including EM energy such as visible light. In an example, the recording electrode can be used with an ERG system to measure an indication of electrical activity in the eye, such as a pattern electroretinography (PERG) test as an indication of ocular blood flow. The recording electrode can include at least one of an electrode that can be in contact with the eye, such as an electrode attached to a contact lens and configured for contact with a surface of the eye, or an electrode in proximity to the eye, such as an electrode that can be located on the lower eye lid of an eye.

The non-invasive ocular imaging system can include a retinal functional imaging (RFI) system. The RFI system can be configured with an energy source capable of generating EM energy at a frequency of about 547 THz (corresponding to a wavelength of about 548 nm). In an example, the RFI system can include a system from Optical Imaging, Ltd. (Rehovot, Israel) offered for sale under the tradename RFI 3000. The RFI system can be configured with an energy source capable of generating EM energy at a frequency of about 666 THz (corresponding to a wavelength of at least 450 nm). In an example, the RFI system can include a system from OcuScience Inc. (Ann Arbor, Mich.) offered for sale under the tradename OcuMet Beacon.

The control circuitry 140 can facilitate and coordinate operation of the apparatus 100. In an example, the control circuitry 140 can be coupled to, such as in communication with, at least one of the fluid regulator 120, the sensor 130, the pressure source 150, or the fluid source 170.

The control circuitry 140 can include a data interface configured to receive a signal, such as at least one of an indication of the eye environment sensed by the sensor 130. In an example, a sensed indication can include at least one of an indication of the eye environment or an indication of a relationship between an indication of a left eye environment and an indication of a right eye environment, such as the sensed indication from the sensor 130. The control circuitry 140 can process the received signal, such as into a processed signal, and transmit the processed signal to one or more components of the apparatus 100.

The control circuitry 140 can be in communication with the fluid regulator 120, such as to adjust the position of the regulator valve to control the working fluid composition. The control circuitry 140 can be in communication with the sensor 130, such as to receive and process an indication of the eye environment including sensed data from the sensor 130. The control circuitry 140 can be in communication with the pressure source 150, such as to generate a pressure source control signal to adjust at least one of working fluid pressure or working fluid flow in the apparatus 100.

The control circuitry 140 can provide a communication interface, such as to allow for a user to operate and interact with the apparatus 100. The communication interface can include a graphical user interface (or GUI), such as communicate information to the user including information on the apparatus 100 (e.g., readout of sensed indications, fault status, etc) or receive information from the user. Information received from the user can include at least one of information to manage basic functionality of the apparatus 100, such as cycling the power to the apparatus 100, or an indication of user preference, such as operational parameters including target levels to define therapeutic protocols and safety parameter such as maximum and minimum limits. In an example, the communication interface can receive a safety pressure level, such as at least one of a maximum or minimum pressure level in the cavity 112 selected by the user to prevent damage to the patient eye, adjusting the working fluid pressure delivered to the cavity 112, or setting a target pressure level in the cavity 112.

The control circuitry 140 can include a digital signal processing (DSP) circuit, such as to receive and record an indication including an indication of the eye environment sensed by the sensor 130, such as at least one of an environmental parameter or a physiological parameter. The indication of the eye environment can be monitored and recorded by the control circuitry 140 for a duration, such as for a period of seconds, minutes, hours, days, years, or for the lifetime of the patient.

The control circuitry 140 can include a processing unit, such as a programmable central processing unit (CPU). The CPU can execute instructions to implement methods of using the apparatus 100, such as to treat, inhibit, or prevent a patient eye condition. In an example, the CPU can be a component of a computing machine, such as a computing machine 1500.

The CPU can be configured as a control circuit, such as a feedback control circuit. The feedback control circuit can receive information, such as at least one of an indication sensed by the sensor 130, an indication of user preference from the communication interface, or an indication of a processed signal including a signal processed by the CPU, and process the sensed indication, such as to form a control signal.

The CPU can be configured as a pressure feedback control circuit, such as to generate a control signal for the pressure source 150 (e.g., a pressure source control signal) to adjust pressure level in the cavity 112, such as based on an indication of cavity pressure level from a pressure sensor in communication with the cavity 112.

In an example, the pressure source control signal can be based on an indication of cavity pressure, such as pressure in the cavity 112, to achieve a target pressure level in the cavity 112. The pressure feedback control circuit can receive an indication of working fluid pressure in the cavity 112, such as an indication of cavity pressure level sensed by the sensor 130 including a pressure sensor in communication with the cavity 112. The pressure feedback control circuit can process the received indication of pressure level to form a control signal, such as a control signal to adjust the pressure source 150 to achieve the target pressure level in the cavity 112.

Processing the received indication of pressure can include calculating an indication, such as calculating an indication of the difference between the indication of cavity pressure level and an indication of user preference, including a cavity pressure setpoint level received from the communication interface to form an indication of a cavity pressure difference value. Processing the received indication can include generating a control signal based on the indication of cavity pressure difference value with a proportional-integral-derivative (PID) control algorithm running on the CPU to adjust the pressure source 150. Generating a control signal can include generating a control signal to minimize the difference between the received indication of pressure level and the cavity pressure setpoint level.

In an example, the pressure source control signal can be based at least in part on an indication of a physiological parameter associated with the patient, such as an indication of IOP in the patient eye, to achieve a target IOP level in the patient eye. The pressure feedback control circuit can receive an indication of IOP level in the patient eye, such as an indication of IOP level sensed by the sensor 130 including a biosensor configured to sense IOP. The pressure feedback control circuit can process the received indication of IOP level to form a control signal, such as a control signal to adjust the pressure source 150, to achieve a target cavity pressure level in the cavity 112, such as a target cavity pressure level sufficient to achieve the target IOP level in the patient eye.

Processing the received indication of IOP can include calculating the difference between the indication of IOP level and an indication of user preference, including an IOP setpoint level received from the communication interface, to form an IOP difference value. Processing the received indication can include generating a control signal based on the IOP difference value with a proportional-integral-derivative (PID) control algorithm running on the CPU to adjust the pressure source 150. Generating a control signal can include generating a control signal to minimize the difference between the received indication of pressure level and the cavity pressure setpoint level.

The CPU can be configured as a concentration feedback control circuit, such as to generate a regulator control signal to adjust a chemical constituent level in the cavity 112.

In an example, the regulator control signal can be based on an indication of a chemical constituent associated with the working fluid, such as an indication of nitric oxide (NO) concentration, to achieve a target NO concentration level in the working fluid. The concentration feedback control circuit can receive an indication of NO concentration level in the working fluid, such as an indication of NO level sensed by the senor 130 including a concentration sensor configured to sense NO. The concentration feedback control circuit can process the received indication of NO level to form a control signal, such as a control signal to adjust the regulator 120 to achieve the target NO concentration level in the cavity 112.

Processing the received indication of NO concentration can include calculating the difference between the indication of NO concentration and an indication of user preference, including a NO setpoint level received from the communication interface, to form a NO difference value. Processing the received indication can include generating a control signal based on the NO difference value. Processing the received indication can include generating a control signal based on the NO difference value with a proportional-integral-derivative (PID) control algorithm running on the CPU to adjust the regulator 120. Generating a control signal can include generating a control signal to minimize the difference between the received indication of NO concentration and the NO setpoint level.

The control circuitry 140 can include pressure source circuitry, such as pressure source circuitry configured to adjust operation of the pressure source 150 based on at least one of an indication sensed by the sensor 130. The pressure source circuitry can include a pressure source logic circuit, such as a pressure source logic circuit configured to generate a system fault based on at least one of a sensed indication received at the data interface or an indication of user preference received through the communication interface. In an example, the pressure source logic circuit can generate a system fault on the occurrence of a fault event, such as when an indication of cavity pressure in the in the cavity 112 exceeds a pressure safety level, such as a pressure safety level set by a user through the communication interface.

The control circuitry 140 can include a power source 152, such as to supply electrical energy to the apparatus 100. In an example, the power source 152 can include a battery, such as a lithium ion battery, and a transformer, such as to receive power from a wall outlet for use in the apparatus 100 at a specified voltage and current. The control circuitry 140 can include a heating element, such as a heating element in communication with the therapeutic fluid including a heating element located on a surface of or in proximity to the cover 110 including an inner surface 188 of the cover 110, or the fluid regulator 120, to increase the temperature of the therapeutic fluid.

The pressure source 150 can generate a volumetric flow of working fluid in the apparatus 100, such as to move working fluid from the pressure source 150 to the cavity 112 or to move working fluid from the cavity 112 to at least one of the pressure source 150 or to the surrounding environment. The pressure source 150 can be configured to apply non-ambient pressure to the cavity 112, such as to adjust an indication of fluid pressure including an indication of pressure level in the cavity 112, from a first pressure level to a second pressure level different from the first pressure level.

The pressure source 150 can include a pump, such as a pump that can generate at least one of a positive gauge pressure or a negative gauge pressure. The pressure source 150 can include an electrically-powered pressure source, such as a pump including a displacement pump or a centrifugal pump. For example, the pressure source 150 can include a diaphragm pump, such as a diaphragm vacuum pump. The pressure source 150 can include a manually-powered pressure source, such as a hand pump including a bellows-style pump. In an example, the pressure source 150 can be integrated into a component of the apparatus 100, such as the cover 110.

Figure 1A:
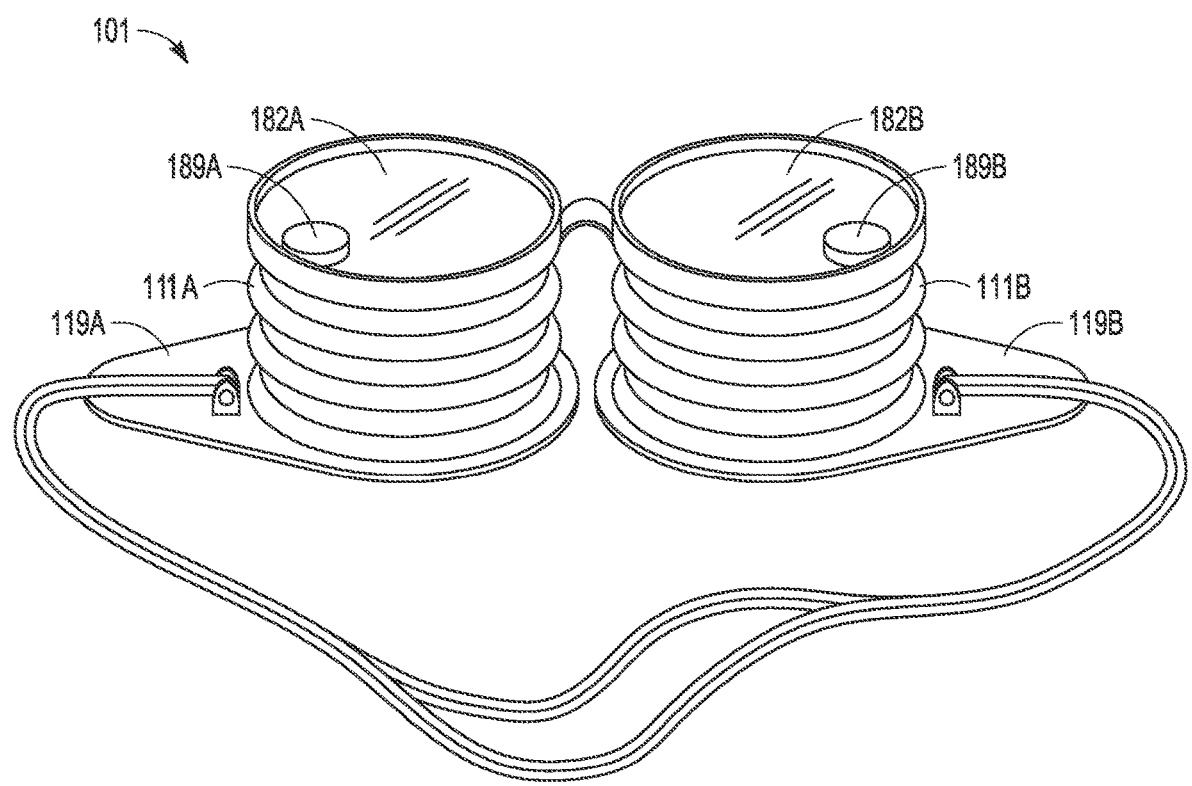
FIG. 1A shows an example of an apparatus including an example of a manually-powered pressure source.

FIG. 1A shows an example of an apparatus 101 including an example of a manually-powered pressure source. In an example, the apparatus 101 can include all the components of the apparatus 100. The apparatus 101 can include a bellows cover 111, such as at least one of a left bellows cover 111A or a right bellows cover 111B, a cavity check valve 189, such as at least one of a left cavity check valve 189A or a right cavity check valve 189B, and a seal 119, such as at least one of a left seal 119A or a right seal 119B.

The bellows cover 111 can be sized and shaped to surround the patient eye and be spaced from the eye, such as without contacting the eye including the anterior surface of the eye. The bellows cover 111 can be sized and shaped to surround and cover both patient eyes, such as the left eye and the right eye of the patient. In an example, the bellows cover 111 can include a mask, such as the bellows cover 111 similar in shape and function to a diving or snorkeling mask.

The bellows cover 111 can include a bellows portion, such as a portion of the bellows cover 111 between the lens 182 and the seal 119. The bellows portion can assume a first bellows position, such as defined by a first bellows distance between the lens 182 and the seal 119. The bellows portion can assume a second bellows position, such as position displaced from the first bellows position. The bellows portion can present a resistance to motion, such as an external force can be required to displace the bellows portion from the first bellows position to the second bellows position. The level of resistance to motion can be controlled, such as through design of the bellows portion including selection of bellows material and number of bellows folds. The bellows portion can display a resilience, such as a tendency of the bellows portion to recover to an equilibrium position including a force equilibrium position after the removal of the external force.

The second bellows position can include a compressed bellows position, such as to generate a negative gauge pressure (e.g., a vacuum) over the patient eye. In an example, the distance between the lens 182 and the seal 119 can be reduced from the first bellows position on the application of a compressive force to the bellows cover 111, such as to the compressed bellows position, to the compressed bellows position. As the bellows cover 111 moves from the first bellows position to the compressed bellows position, the volume of the cavity 112 can be reduced, such as to increase working fluid pressure in the cavity 112, after which the cavity 112 can expel a volume of working fluid from the cavity 112, such as through the check valve 189. On removal of the compressive force, the bellows portion can recover to a third bellows position, such as a position between the first and compressed bellows positions, due to the resilience of the bellows portion, such as to create a "suction" or negative gauge pressure over the patient eye.

The second bellows position can include an extended bellows position, such as to generate a positive gauge pressure (e.g., an increase in pressure as compared to ambient pressure) over the patient eye. In an example, the distance between the lens 182 and the seal 119 can be increased from the first bellows position on the application of an extension force to the bellows cover 111, such as to the extended bellows position. As the bellows cover 111 moves from the first bellows position to the extended bellows position, the volume of the cavity 112 can be increased, such as to decrease working fluid pressure in the cavity 112, after which the cavity 112 can receive a volume of ambient air from the surrounding environment, such as through the check valve 189. On removal of the extension force, the bellows portion can recover to a third bellows position, such as a position between the first and extended bellows position, due to the resilience of the bellows portion, such as to create a "pressurized" or positive gauge pressure over the patient eye.

The pressure source 150 can include a source of pressure, such as a pressurized gas cylinder or a source of pressurized fluid separate from the apparatus 100 that can be used to adjust working fluid pressure in the cavity 112. The pressure source 150 can include a source of pressure used in combination with a supplementary device to adjust pressure in the cavity. In an example, the pressure source 150 can include a venturi-type pump, such as a venturi jet pump, in communication with the source of pressure to adjust fluid pressure in the cavity 112.

The pressure source 150 can be characterized by physical characteristics, such as a relationship between physical characteristics. A useful measure for comparing the performance of several sources of flow includes a volume-pressure characteristic, such as the relationship between the volume of working fluid flow from a source of flow and the pressure, such as static pressure, created due to the fluid flow. In an example, the pressure source 150 can be characterized by a volume-pressure characteristic, such as a p-Q chart.

The pressure source 150 can generate a pressure in the cavity 112, such as to adjust pressure in the cavity 112 to move towards or achieve a target cavity pressure in the cavity 112. The target cavity pressure can include the cavity pressure to affect a measurement procedure including a diagnostic procedure on the patient eye. In an example, pressure in the cavity 112 can be adjusted with the pressure source 150 towards a target cavity pressure, such as a first target cavity pressure to affect a first displacement of an anterior surface of the patient eye. An indication of the first displacement can be sensed by a sensor 130 including a displacement sensor. Subsequently, a second target cavity pressure can affect a second displacement of the anterior surface of the patient eye, such as an indication of the second displacement that can be sensed by the displacement sensor. The difference between the indications of displacement at the first and second target pressure can result in an estimate of a physiological parameter, such as an estimate of an indication of IOP in the patient eye.

The target cavity pressure can include the cavity pressure to affect a treatment of the patient eye, such as a cavity pressure prescribed by a medical professional to treat, inhibit, or prevent an eye condition. In an example, pressure in the cavity 112 can be adjusted with the pressure source 150 toward a target cavity pressure, such as a target cavity pressure to affect an indication of a physiological parameter of the patient eye including an indication of IOP level in the patient eye that can be sensed by a sensor 130 including a biosensor configured to sense an indication of IOP. Treatment of the patient eye can be affected by the pressure source 150, such as by adjusting the pressure source to achieve a target cavity pressure in the cavity 112 to affect a desired indication of IOP level in the patient eye.

The target cavity pressure can include a target IOP cavity pressure, such as a pressure applied to the cavity 112 to achieve a target IOP level in the patient eye. A target IOP cavity pressure can include a cavity pressure that can adjust or achieve an IOP level in a patient eye, such as to increase or decrease the IOP level in the patient eye. A target IOP level can include an IOP level in a range of about 5 mmHg to about 30 mmHg, an IOP level in a range of about 10 mmHg to about 21 mmHg, and an IOP level in a range of about 12 mmHg to about 18 mmHg.

Translaminar pressure describes the pressure differential across the lamina cribrosa. The translaminar pressure difference (TPD) can be defined as the difference between intraocular pressure in the patient eye and cerebrospinal fluid pressure in the patient body. Translaminar pressure gradient (TPG) is related to TPD and can be defined as the difference between IOP and CSFP per unit thickness of the lamina cribrosa. An indication of TPD, such as TPD level, can indicate the physiological health of the patient eye, such as the presence or absence of an eye condition. A physiologically normal eye, such as a patient eye in the absence of an eye condition, can be characterized by a normal TPD level, such as normal TPD level in at least one of a range of about −4 mmHg to about 4 mmHg or a range of about −6 mmHg to about 6 mmHg. In contrast, a non-normal eye, such as a patient eye experiencing an eye condition including glaucoma, can be characterized by a TPD level that falls outside the range of normal TPD level, such as the TPD level can be less than about −4 mmHg or greater than about 4 mmHg.

The target cavity pressure can include a target equalization cavity pressure, such as the pressure applied to the cavity 112 that can equalize TPD level in an eye. A cavity pressure that can equalize TPD level in the eye can include any pressure applied to the cavity 112 that can reduce TPD level in the eye, such as from a first TPD level to a second TPD level including where the absolute value of the second TPD level can be less than the absolute value of the first TPD level.

The target cavity pressure can include a target translaminar pressure difference (TPD) cavity pressure, such as a pressure applied to the cavity 112 that can achieve a target TPD level in the patient eye. A target TPD cavity pressure can include the pressure level applied to the cavity 112 sufficient to adjust the TPD level of a patient eye into a range, such as a target TPD level range. A target TPD level range can include a TPD level in a range of at least one of about −4 mmHg to about 4 mmHg, about −6 mmHg to about 6 mmHg, about −7 mmHg to about 7 mmHg, or about −10 mmHg to about 10 mmHg. In an example, a normal TPD level range can include a TPD level in a range of at least one of about −4 mmHg to about 4 mmHg or about −6 mmHg to about 6 mmHg.

Adjusting TPD, such as adjusting TPD in the patient eye from a first TPD level to a second TPD level lower than the first TPD level, can improve physiological processes in the patient eye, such as to improve the health of the patient eye. Axonal transport, such as the collection of cellular processes responsible for maintaining cell viability in the patient optic nerve, can be adversely affected in the presence of elevated TPD, such as where the indication of TPD in the patient eye does not fall within the normal TPD level range. Indications of axonal transport level, such as in the optic nerve, can be sensed by the sensor 130 including an axonal transport sensor. In an example, an axonal transport sensor can include at least one of an optical coherence tomography (OCT) imaging system or a confocal scanning laser ophthalmoscope (CSLO) system.

The target cavity pressure can include a target axonal transport cavity pressure, such as a cavity pressure applied to the cavity 112 to achieve a target axonal transport level in the patient eye. A target axonal transport cavity pressure can include a cavity pressure that can enhance (or increase) an indication of axonal transport level in an eye, such as from a first indication of axonal transport level to a second indication of axonal transport level where the indication of second axonal transport level can be greater than the indication of first axonal transport level.

Rates of axonal transport can vary, such as based on the physiological constituents transported. In an example, "slow" axonal transport can represent the movement of cytoplasmatic constituents along an axon, such as including cytoskeletal and soluble enzymes of intermediary metabolism. A target axonal transport level, such as for slow axonal transport constituents, can include an axonal transport level in a range of about 0.2 mm/day to about 2 mm/day. In an example, "fast" axonal transport can represent the movement of mitochondrial polypeptides and neuropeptides, such as synaptic vesicle polypeptides, along an axon. A target axonal transport level, such as for fast axonal transport constituents, can include an axonal transport level in a range of about 50 mm/day to about 100 mm/day, such as for mitochondrial polypeptides, and an axonal transport level in a range of about 100 mm/day to about 200 mm/day, such as for neuropeptides.

A target cavity pressure can include a target therapeutic cavity pressure to treat, inhibit, or prevent an eye condition in the patient eye.

A target therapeutic cavity pressure to treat an eye condition can include a cavity pressure selected to adjust an indication of a physiological parameter, such as a physiological parameter sensed by the sensor 130. In an example, adjusting an indication of a physiological parameter can include relieving a patient symptom, such as relieving patient discomfort, or improving patient function, such as patient function degraded due to an eye condition or a disease state.

A target therapeutic cavity pressure to inhibit an eye condition can include a cavity pressure selected to maintain patient function, such as to stop or delay further degradation of patient function due to a diagnosed eye condition. In an example, maintaining an indication of patient function can include minimizing variation in an indication of a physiological parameter of the patient eye. For example, a target therapeutic cavity pressure to inhibit an eye condition can include a cavity pressure selected to minimize variation in an indication of IOP over a period of time.

A target therapeutic cavity pressure to prevent an eye condition can include a cavity pressure selected as a prophylactic measure applied to a patient eye prior to the appearance of an eye condition. In an example, for a patient presenting with a precursory characteristic for an eye condition, such as an abnormal cup-to-disc ratio as a potential indication of glaucoma, a cavity pressure can be applied to the patient eye with the apparatus 100, such as at a pressure level suitable for the patient physiology, to prevent physiological processes from progressing to a clinical eye condition diagnosis. Thus, a target cavity pressure level can include a cavity pressure level sufficient to adjust the cup-to-disc ratio in a patient eye from a first cup-to-disc ratio to a second cup-to-disc ratio lower than the first cup-to-disc ratio, such as to reduce the cup-to-disc ratio in the patient eye.

The conduit 117 can provide a patent fluidic transmission path between one or more components of the apparatus 100, such as a continuously patent fluidic transmission path between at least one of the cavity 112 and the sensor 130 or the cavity 112 and the pressure source 150. The conduit 117 can include a lumen, such as one or more lumens.

Figure 5A:
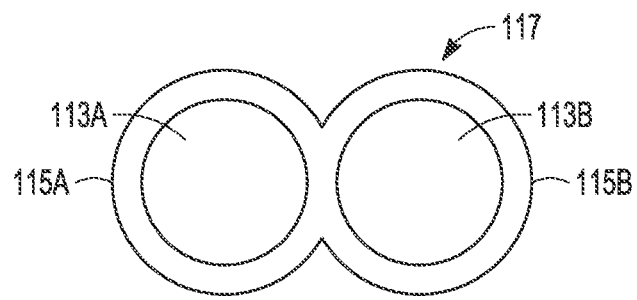
FIG. 5A shows a cross-section of an example first dual lumen conduit.

FIG. 5A shows a cross-section of an example of a conduit 117, such as a first dual lumen conduit. The first dual lumen conduit can include a first lumen 113A defined by a first lumen wall 115A and a second lumen 113B defined by a second lumen wall 115B, such as the first lumen 115A can be located adjacent to the second lumen 115B. In an example, the first lumen 113A can provide a fluid communication path between the pressure source 150 and the cavity 112, such as the pressure source 150 can transfer working fluid to the cavity 112 through the lumen 113A to achieve a target cavity pressure level. In an example, the second lumen 113B can provide a fluidic communication path between the cavity 112 and the sensor 130, such as the working fluid pressure sensor located on the control circuitry 140, to allow the sensor 130 to sense an indication of cavity pressure level in the cavity 112, such as for use as a feedback signal to control operation of the pressure source 150.

A potential operational hazard of the apparatus 100 can include a blockage in the conduit 117, such as a state of the conduit 117 where the patent fluidic transmission path can be interrupted, including a kink in the conduit 117. In an example, a kink can include a blockage, such as a blockage due to a bending force applied to the conduit 117 that can cause at least one of the first lumen 113A or the second lumen 113B to fold over and collapse on itself, such as a first portion of an inner surface of the lumen can contact a second portion of the inner surface of the lumen to prevent fluid transmission through the lumen. A kink in the conduit 117 between the cavity 112 and the sensor 130, such as the working fluid pressure sensor located on the control circuitry 140, can create a potential for the pressure source 150 to run out of control, such as the control circuitry 140 can command the pressure source 150 to generate a cavity pressure level based on an erroneous indication of cavity pressure level from the sensor 130.

In an example, a kink in the first lumen 113A can stop fluidic communication between the cavity 112 and the working fluid pressure sensor, such as to cause the working fluid pressure sensor to sense an erroneous indication of cavity pressure level including a state of no cavity pressure level (e.g., an indication of cavity pressure level of about 0 mmHg gauge). The erroneous indication of cavity pressure level can cause the control circuitry 140 to command the pressure source 150 to adjust, such as increase or decrease, fluid transfer to the cavity 112, such as to operate the pressure source 150 to compensate for cavity pressure level in the cavity 112, such as to achieve or maintain the target cavity pressure level. Continued sensing of the erroneous indication of cavity pressure level can cause the pressure source 150 to operate in a "run-away" (or uncontrolled) state, such as to potentially generate cavity pressure levels that could damage the patient eye. To avoid a run-away state, the conduit 117 can include a feature, such as one or more features, designed to enhance the safety of the apparatus 100, such as the operational safety of the apparatus 100 due to a blockage including a kink in the conduit 117.

Figure 5B:
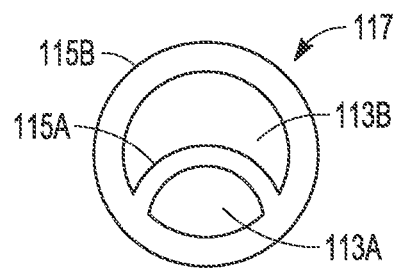
FIG. 5B shows a cross-section of an example second dual lumen conduit.

FIG. 5B shows a cross-section of an example of a second dual lumen conduit, such as a conduit 117 where the first lumen wall 115A can interface with the second lumen wall 115B, such as to form a first lumen 113A and a second lumen 113B within the second lumen wall 115B.

Figure 5C:
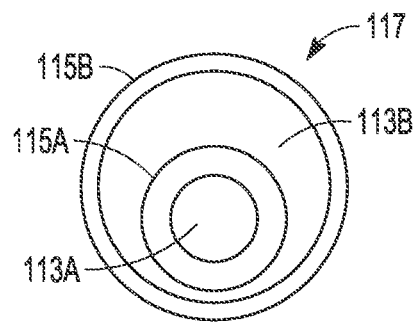
FIG. 5C shows a cross-section of an example third dual lumen conduit.

FIG. 5C shows an example of a third dual lumen conduit, such as a conduit 117 where the first lumen 113A can be located completely within the second lumen 113B, such as the first lumen wall 115A can be separate from the second lumen wall 115B.

Patency of the conduit 117 can be controlled, such as by orientation of the first lumen 113A with respect to the second lumen 113B. In an example, a kink in the conduit 117, such as at least one of the example conduit 117 shown in FIG. 5B or FIG. 5C, can block the first lumen 113A, such as to prevent fluid transfer from the pressure source 150 to the cavity 112, but allow the second lumen 113B to remain open, such as an outer surface of the first lumen wall 115A can prevent the second lumen 113B from collapsing on itself, such as by preventing a first portion of the inner surface of the second lumen 113B from contacting a second portion of the inner surface of the second lumen 113B.

Patency of the conduit 117 can be controlled, such as by design of the conduit 117, including design of at least one of the first lumen 113A or the second lumen 113B. Dimensions of conduit 117 can be selected, such as to maintain patency of the second lumen 113B. In an example, the thickness of the first lumen wall 115A can be different from the thickness of the second lumen wall 115B, such as to prevent a first portion of the second lumen 113B from collapsing on itself, such as when subjecting the conduit 117 to a bending force. Materials used to construct the conduit 117 can be selected, maintain patency of the second lumen 113B. In an example, the type or durometer of the material used to form the first lumen wall 115A can be different from the type or durometer of the material used to form the second lumen wall 115B, such as to prevent a first portion of the second lumen 113B from collapsing on itself, such as when subjecting the conduit 117 to a bending force.

The conduit 117 can include a reinforcing structure, such as to prevent blockage of at least one of the first lumen 113A or the second lumen 113B. The reinforcing structure can include a coil of wire, such as a wire coil located in the first lumen wall 115A or the second lumen wall 115B and extending around the periphery of at least one of the first lumen wall 115A or the second lumen wall 115B.

The cross-sectional shape of the conduit 117 can assume a shape, such as any shape without affecting the function of the conduit 117. The cross-sectional shape of the conduit 117, such as the cross-sectional shape of the first lumen 113A and the cross-sectional shape of the second lumen 113B, can include at least one of a circular, oval, crescent, triangular, rectangular, or any polygonal cross-section shape.

Flexibility of the conduit 117, such as the overall stiffness of the conduit 117 due to the stiffness of the first lumen wall 115A and the second lumen wall 115B, can be controlled. In an example, a structural configuration of the conduit 117, such as a structural configuration that minimizes a moment of inertia associated with the cross-sectional shape of the conduit 117, can reduce the stiffness of the conduit 117. For example, a first dual lumen conduit, such as with a first moment of inertia, can demonstrate higher overall stiffness, such as in bending or in torsion, when compared to at least one of a second dual lumen conduit with a second moment of inertia or a third dual lumen conduit with a third moment of inertia, such as where the first moment of inertia can be greater than the second or third moments of inertia. In an example, the second dual lumen conduit or the third dual lumen conduit can minimize torsional bias, such as torsional bias that can result from at least one of bonding or extruding, as compared with the first dual lumen conduit.

The apparatus 100 can affect an intraocular structure of the eye, such as by adjusting the eye environment in contact with the anterior surface of the patient eye. In an example, applying non-ambient pressure to an anterior surface of the eye can adjust IOP in the eye, such as to generate forces that can be reacted by an intraocular structure of the eye. An intraocular structure can include at least one of a retina, a choroid, or a blood vessel including one or more intraocular blood vessels that can perfuse the intraocular structures. In reacting applied forces, a characteristic of the intraocular blood vessel, such as a blood vessel parameter, can be adjusted or otherwise changed in response to the applied force.

A blood vessel parameter can describe a characteristic associated with the blood vessel and can include at least one of vessel caliber (e.g., vessel diameter), such the change of vessel caliber associated with a spontaneous venous pulsation (SVP) including a dynamic vessel caliber variation, vessel shape, such as the shape of a cross-sectional area, vessel color, or blood flow in the vessel, such as at least one of blood flow volume or blood flow velocity. By adjusting forces applied to the intraocular structure, such as by adjusting non-ambient pressure applied to an anterior surface of the eye, the apparatus 100 can adjust one or more blood vessel parameters.

The apparatus 100 can include a blood flow apparatus (or BFA), such as to adjust blood flow in a patient eye. The BFA can include a cover 110, a fluid regulator 120, a sensor 130, control circuitry 140, and a pressure source 150.

The control circuitry 140 can be configured to adjust blood flow in the patient eye. For example, the control circuitry 140, in communication with the pressure source 150, can be configured to adjust fluid pressure in the cavity to regulate ocular blood flow, such as toward a target level including a target level of blood flow. The control circuitry 140 can receive an indication of a blood vessel parameter from a blood vessel in the eye and process the received indication, such as to adjust working fluid pressure in the cavity 112 (e.g., cavity pressure) to adjust blood flow in the patient eye based at least in part on the received indication.

The control circuitry 140 can include a central processing unit (CPU) that can be configured as a feedback control circuit, such as to generate a control signal for the pressure source 150 (e.g., a pressure source control signal). The pressure source control signal can cause the pressure source 150 to adjust working fluid pressure level in the cavity 112, such as based at least in part on the received indication including the blood vessel parameter.

The pressure source control signal can be based at least in part on the indication of the blood vessel parameter, such as an indication of blood flow in the blood vessel that can be sensed by a blood flow sensor. The CPU can execute a pressure source adjustment cycle, such as series of actions to adjust cavity pressure applied to an anterior surface of the eye as described in the steps that follow.

In an example of the pressure source adjustment cycle, the CPU can receive the sensed indication of blood flow, such as a first indication of blood flow. The CPU can generate a pressure source control signal, such as based at least in part on the indication of blood flow, to adjust the pressure source 150 to incrementally adjust the non-ambient pressure applied to the cavity 112, such as to adjust blood flow in the vessel. The CPU can receive a second indication of blood flow, such as an indication of blood flow resulting from the incremental application of non-ambient pressure to the cavity 112. The CPU can compare the received indications, such as the first and second received indications, and adjust the applied non-ambient pressure, such as to increase or decrease the non-ambient pressure, based on the difference between the first and second received indications. The pressure source adjustment cycle can be executed multiple times until a target criterion is satisfied.

A target criterion can include a target blood flow level, such as a blood flow level selected to treat an eye condition, such as to restore eye perfusion to a "normal" level of blood flow. In an example, a normal blood flow level can be characterized in terms of a total retinal blood flow rate (TRBFR), such as TRBFR in a range of about 68 µl/min to about 92 µl/min (e.g., 80 µl/min+/−12 µl/min). The CPU can compare the received indication, such as the sensed indication of blood flow to the target blood flow level and adjust the pressure source 150 to apply non-ambient pressure to the cavity 112, such as to adjust TOP in the eye to affect blood flow in the eye toward the target blood flow level.

The target blood flow level can include a blood flow level selected to maximize blood flow level in a patient eye subject to a target TOP level. In an example, a target TOP level can include an TOP level in at least one of a range of about 5 mmHg to about 30 mmHg, a range of about 10 mmHg to about 21 mmHg, and a range of about 12 mmHg to about 18 mmHg. The CPU can generate a test pressure source signal, such as to apply a range of non-ambient test pressure levels to the cavity 112 in an incremental manner, while simultaneously monitoring the concomitant blood flow level for each incremental test pressure level. The CPU can thereafter select and apply a pressure source control signal to the pressure source 150, such as to achieve the pressure level in the target TOP range associated with the greatest blood flow level.

Organ perfusion, such as the delivery of blood flow sufficient to maintain cell viability, is required for tissue health and general well-being. Perfusion can depend on a pressure difference across the perfused organ, such as an arteriovenous pressure difference. Ocular perfusion pressure (or OPP) can be characterized as a relationship between blood pressure (BP), such as systemic BP of the patient, and intraocular pressure (IOP) in the patient eye. In an example, an OPP level can be defined as the difference between BP level and IOP level, such as OPP=BP−IOP. In an example, an OPP level including a mean OPP level can be defined as MOPP=⅔*(MAP−IOP), such as where MAP=mean arterial pressure=DBP+⅓*(SBP−DBP), where SBP is systolic blood pressure and DBP is diastolic blood pressure.

The systemic BP of a patient can vary greatly with the activity level of the patient, such as to affect the OPP level in the patient eye. Inadequate OPP can result in abnormal ocular metabolic activity, such as reduced metabolic activity, or ischemic damage that can lead to retinal cell apoptosis, such as to induce or exacerbate a chronic eye condition including glaucoma.

The target blood flow level can include a blood flow level selected to maximize blood flow level in a patient eye subject to a target OPP level. In an example, a target OPP level can include at least one of a range of about 30 mmHg to about 70 mmHg, a range of about 40 mmHg to about 60 mmHg, and a range of about 45 mmHg to about 55 mmHg. The CPU can generate a test pressure source signal, such as to apply a range of non-ambient test pressure levels to the cavity 112 in an incremental manner, while simultaneously monitoring the concomitant blood flow level for each incremental test pressure level. The CPU can thereafter select and apply a pressure source control signal to the pressure source 150, such as to achieve the pressure level in the target OPP range associated with the greatest blood flow level.

The target blood flow level can include a blood flow level selected to adequately perfuse ocular tissue independent of patient activity level, such as a target ocular perfusion pressure (OPP) level. In implementing a target blood flow level, the control circuit 140 can receive an indication of blood flow, an indication of systemic BP, and an indication of IOP, and process the received indications, such as to adjust fluid pressure in the cavity based on at least one of the received indications.

In an example, a pressure source adjustment cycle based on an indication of OPP can be executed. The CPU can receive the sensed indications of IOP and blood pressure to form an indication of OPP, such as a first indication of OPP. The CPU can generate a pressure source control signal, such as based on the indication of blood flow, to adjust the pressure source 150 to apply non-ambient pressure to the cavity 112, such as to adjust blood flow in the vessel. The CPU can receive a second indication of blood flow, such as an indication of blood flow resulting from the application of non-ambient pressure to the cavity 112. The CPU can compare the received indications, such as the first and second received indications, and adjust the applied non-ambient pressure. The pressure source adjustment cycle can be executed multiple times until a target criterion is satisfied.

Figure 6:
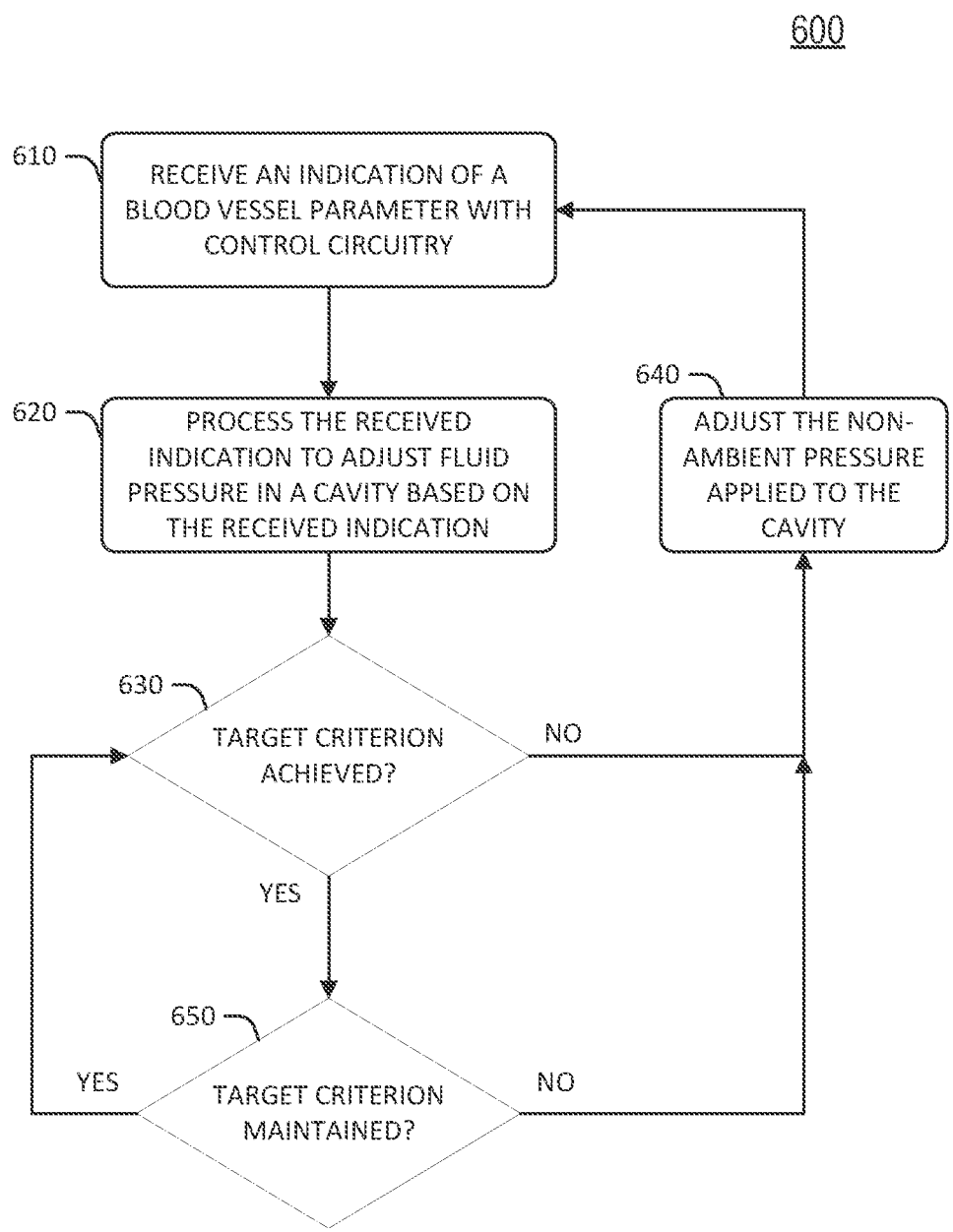
FIG. 6 shows an example method for using the apparatus to adjust blood flow in an ocular vessel of a patient eye.

FIG. 6 shows an example method 600 for using the apparatus 100 to adjust blood flow in an ocular vessel of a patient eye. The control circuitry 140 can be configured to receive an indication of a blood vessel parameter from a blood vessel in the eye and process the received indication to adjust fluid pressure in the cavity 112 based at least in part on the received indication. In an example, the control circuitry 140 can adjust the blood flow in the eye from a first indication of blood flow to a second indication of blood flow, such as to improve perfusion of ocular tissue.

At 610, an indication of a blood vessel parameter can be received, such as with the control circuitry 140. Receiving the indication can include receiving an indication of blood flow, such as at least one of blood flow volume or blood flow velocity, in an ocular blood vessel.

Receiving the indication can include receiving an indication of at least one of an environment parameter or a physiological parameter associated with the eye. Receiving the indication can include receiving an indication of fluid pressure in the cavity 112, such as with a pressure sensor. Receiving the indication can include receiving an indication of intraocular pressure (IOP) in the eye, such as with an TOP sensor. Receiving the indication can include receiving an indication of systemic blood pressure (BP) in the patient, such as with a BP sensor.

Receiving the indication can include receiving an indication from a user, such as a person or machine interacting with the apparatus 100. Receiving an indication from the user can include receiving user input, such as through the GUI in communication with the control circuitry 140. In an example, user input can include a target level, such as at least one of a target criterion including a target blood flow level and a target OPP level, or other input associated with operation of the apparatus 100.

Receiving the indication can include receiving a target OPP level, such as an OPP level specified by a medical professional to adjust ocular tissue perfusion in the patient. The target OPP level can include a target OPP level to maintain sufficient blood flow in the eye, such as to inhibit, treat, or prevent an eye condition.

At 620, the received indication of the blood vessel parameter can be processed, such as with the control circuitry 140, to adjust fluid pressure in the cavity 112 based at least in part on the received indication.

Processing the received indication can include displaying the indication of the received indication, such as the indication of the blood vessel parameter, to the user. Display can occur through a graphical user interface (GUI), such as through a GUI in communication with the control circuitry 140. In an example, a user can adjust the apparatus 100 manually, such as by visualizing a representation of the received indication on the GUI and manually adjusting the pressure source 150, toward a target criterion based on the received blood vessel parameter indication.

Processing the received indication can include calculating an indication, such as based on at least one of the received indications. Calculating an indication can include calculating an indication of ocular perfusion pressure (OPP), such as based at least in part on a received indication of IOP level and a received indication of systemic BP level. An indication of systemic BP level can include an indication of systolic BP level and an indication of diastolic BP level.

Processing the received indication can include forming a feedback signal, such as a feedback signal configured to adjust the pressure source 150. In an example, the feedback signal can include the pressure source control signal. The feedback signal can be based at least in part at least one of the received indication or the calculated indication. In an example, the control circuitry 140 can adjust the pressure source 150 automatically, such as through a feedback loop running on the control circuitry 140, toward a target criterion based at least in part on the received blood vessel parameter indication.

At 630, achievement of a target criterion can be identified, such as with the control circuitry 140. The target criterion can be defined by a relationship, such as a relationship between the received indications. In an example, the relationship can include a target differential value, such as the difference between an indication of a parameter sensed by the sensor 130 and a target level specified by a user.

The target criterion can be achieved when the target criterion falls within a target range. If the target criterion falls within the target range, the control circuitry 140 can generate a null (e.g., zero) pressure source control signal, such as to cease adjustment of the pressure source 150. If the target criterion does not fall within the target range, the control circuitry 140 can generate a non-zero pressure source control signal, such as to adjust the pressure source 150 to change the fluid pressure in the cavity 112 to achieve a target level in the target range.

In an example, identifying achievement of a target blood flow level can include calculating a target differential blood flow value. The target differential blood flow value can be defined as the difference between a target blood flow level and a received indication of blood flow from an ocular flow sensor. The target blood flow level can be achieved when the target differential blood flow value falls within a target blood flow range, such as total retinal blood flow rate (TRBFR) in a range of about 68 µl/min to about 92 µl/min (e.g., 80 µl/min+/−12 µl/min).

In an example, identifying achievement of a target OPP level can include calculating a target OPP value. The target OPP value can be defined as the difference between a target OPP level and a calculated indication of OPP level. The target OPP level can be achieved when the target OPP value falls within a target OPP value range, such as a range of OPP levels centered about the target OPP value. In an example, a target OPP value range can include at least one of a range of about −15 mmHg to about 15 mmHg, a range of about −10 mmHg to about 10 mmHg, and about −51 mmHg to about 5 mmHg.

At 640, the non-ambient pressure level applied to the cavity 112 can be adjusted. Adjusting the non-ambient pressure level in the cavity 112 can include adjusting an environmental parameter, such as the working fluid pressure in the cavity 112 with the pressure source 150. Adjusting the non-ambient pressure level can include generating the pressure source control signal with the control circuitry 140. The pressure source control signal can be based at least in part on an indication associated with the control circuitry 140, such as at least one of the received indication or the calculated indication. The level of non-ambient pressure adjustment can be modified, such as by adjusting a physiological parameter in the patient including at least one of patient TOP or CSFP. The physiological parameter can be adjusted, such as by administering medication that can increase or decrease at least one of TOP or CSFP in the patient.

At 650, maintenance of the target criterion can be identified, such as with the control circuitry 140. Maintaining the target criterion can include identifying when the target differential value falls within the target range over a duration of time. A duration of time can include the period of time the apparatus 100 can be used by the user. If the target criterion falls within the target range, the control circuitry 140 can generate a null (e.g., zero) pressure source control signal, such as to cease adjustment of the pressure source 150. If the target criterion does not fall within the target range, the control circuitry 140 can generate a non-zero pressure source control signal, such as to adjust the pressure source 150 to change the fluid pressure in the cavity 112 to achieve a target level in the target range. Maintaining the target criterion can include calculating a target OPP value and identifying when the target OPP value falls within the target OPP range.

Autoregulation can be defined as an intrinsic ability of an organ to maintain a constant flow of blood through the organ to meet metabolic demands despite variations in arterial and venous pressures. Autoregulation capability, such as ocular autoregulation (OA) capability, can refer to the ability of an eye to maintain a constant flow of blood through the eye, such as subject to variations in pressure across the eye including variations in OPP.

Figure 7A:
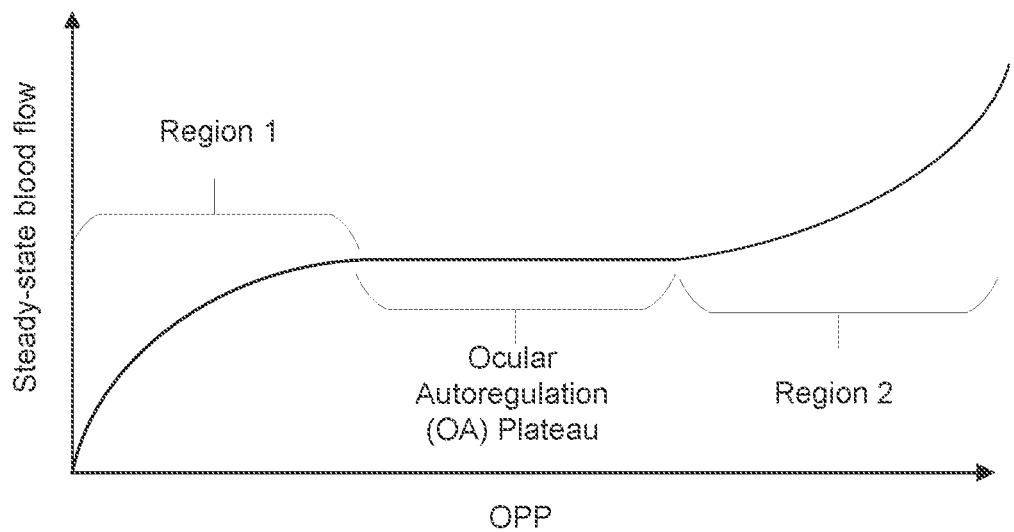
FIG. 7A shows a graph illustrating a first example of AR capability in an eye.

FIG. 7A shows a graph illustrating a first example of OA capability in an eye, such as a physiologically normal eye. The ocular autoregulation (OA) plateau indicates that for a range of OPP level, such as a range that can depend on the unique physiology of each patient, the eye can maintain a constant blood flow, such as a constant volumetric (or "steady-state") blood flow, to adequately perfuse the eye. In an example, the OA plateau can be considered an optimal level of blood flow to adequately perfuse eye tissue. In contrast, for an OPP level located outside the OA plateau, such as the OPP level in Region 1 or Region 2, the eye cannot maintain constant blood flow in the eye, such as the blood flow in the eye can depend on the OPP level experienced by the eye. Reduced blood flow level, such as experienced in Region 1 at low OPP levels, that fall below the threshold level of blood flow required to adequately perfuse eye tissue can cause damage to the eye, such as ischemic damage that can contribute to the genesis or progression of an eye condition including glaucoma.

The size of the OA plateau, such as the range of OPP levels defining the OA plateau, can predict a predisposition for or indicate the presence of an eye condition. In an example, a "small" OA plateau (as compared to the OA plateau in a physiologically normal eye) or the absence of an OA plateau can indicate the presence of an eye condition, such as before a patient becomes symptomatic. Thus, assessment of OA capability in the eye can be a useful clinical tool for the diagnosis and treatment of an eye condition.

Figure 7B:
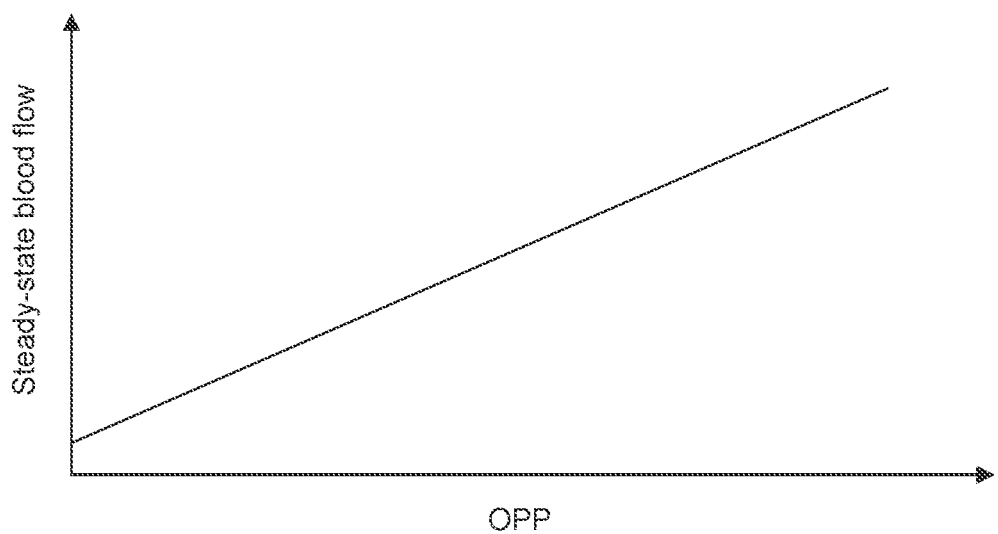
FIG. 7B shows a graph illustrating a second example of AR capability in an eye.

FIG. 7B shows a graph illustrating a second example of OA capability in an eye, such as displaying the absence of an OA plateau that can indicate a physiologically dysfunctional eye. In an eye experiencing an eye condition, the OA capability graph can demonstrate blood flow dependent on OPP level in the eye, such as linearly dependent on OPP level over a range of OPP levels. As a result, the range of OPP level to maintain the optimal level of blood flow to adequately perfuse eye tissue can be greatly reduced, such as compared to the OA capability in the physiologically normal eye shown in FIG. 7A.

The absence of an OA plateau can be of great concern for the health of a patient eye. Natural variations in physiological pressure level, such as system blood pressure and TOP, can cause the OPP level in a patient eye to vary during a daily 24-hour cycle. For example, reduced OPP level at night, such as during sleep when patient systemic BP can be reduced and TOP can be increased due to body position, can reduce blood flow to the patient eye which can result in an ischemic condition, potentially creating or exasperating an eye condition.

The ability to adjust OPP for diagnostic purposes, such as to identify an abnormal OA capability in an asymptomatic patient, can allow a medical professional to prescribe prophylactic measures, such as to identify an eye condition and prescribe a treatment regimen to maintain optimal perfusion of ocular tissue. Since the range of OPP level to maintain threshold blood perfusion in an eye with an eye condition can be much smaller than the range of OPP level in a physiologically normal eye, identification of OA capability can be of great importance in the identification and treatment of an eye condition.

The apparatus 100 can include an ocular autoregulation apparatus (or OAA), such as to identify an indication of ocular autoregulation (OA) capability in a patient eye. The OAA can include a cover 110, a fluid regulator 120, a sensor 130, control circuitry 140, and a pressure source 150.

The control circuitry 140 can be configured to process an indication of OA capability including an ocular autoregulation (OA) index. The control circuitry 140 can receive an indication of a blood vessel parameter from a blood vessel in the eye and process the received indication, such as to form an ocular autoregulation (OA) value.

The control circuitry 140 can include a CPU configured as a data processing circuit, such as to receive an indication, including one or more indications from one or more sensor 130 associated with the apparatus 100, and process the received indications, such as to provide an indication of a relationship between the received indications. The relationship can be characterized by an independent variable and an associated dependent variable, such as to form an OA value.

The OA value can be defined as a relationship between an independent variable and an associated dependent variable, such as to form an ordered pair of received indications. In an example, the OA value can include an OPP level (independent variable) and the blood flow level in the patient eye associated with the OPP level (dependent variable). An OA value can include a first OA value, such as a first ordered pair of a first OPP level and a first blood flow level associated with the first OPP level, and a second OA value, such as a second ordered pair of a second OPP level and a second blood flow level associated with the second OPP level.

The control circuitry 140 can be configured to adjust the pressure in the cavity toward a target level, such as toward a target OA mark level. The target OA mark level can include the independent variable of an OA value, such as an independent variable specified by a user of the apparatus 100. The target OA mark level can include a target OPP graph-point level, such as an OPP level selected by the user as the basis to form an OA value for use in an OA capability graph. In an example, one or more OA capability graphs can be generated over time, such as OA capability graphs with the same target OA mark level, to allow the user to compare one or more OA capability graphs with a point-by-point inspection, such as to identify a change in OA capability over time. In an example, two or more OA values can form an OA capability graph, such as with uniform increments (e.g., uniform target OA mark levels) between independent variables.

The control circuitry 140 can be configured to process an ocular autoregulation (OA) index. A collection of two or more OA values can define an OA capability line, such as a line characterizing the OA capability of the eye over a range of OPP levels. An OA capability line can be characterized by an OA index, such as a characteristic of the OA capability line. An OA index can include at least one of a slope of the OA capability line or the length of the OA capability line, such as the length of a portion of the OA capability line with a specified slope.

In an example, the control circuitry 140 can be configured to calculate the slope of a best-fit line between at least two OA values, such as to form an OA index for the patient eye based on the OA values. In an example, a best-fit line can include a linear regression selected to minimize error in a least mean squares (LMS) sense, such as to minimize the sum of the squares of the residuals. The OA index from the patient eye can be compared to a composite OA index, such as a composite OA index compiled from epidemiological data or a range of OA indices associated with an eye condition, to identify an eye condition, such as in an asymptomatic patient.

Figure 8:
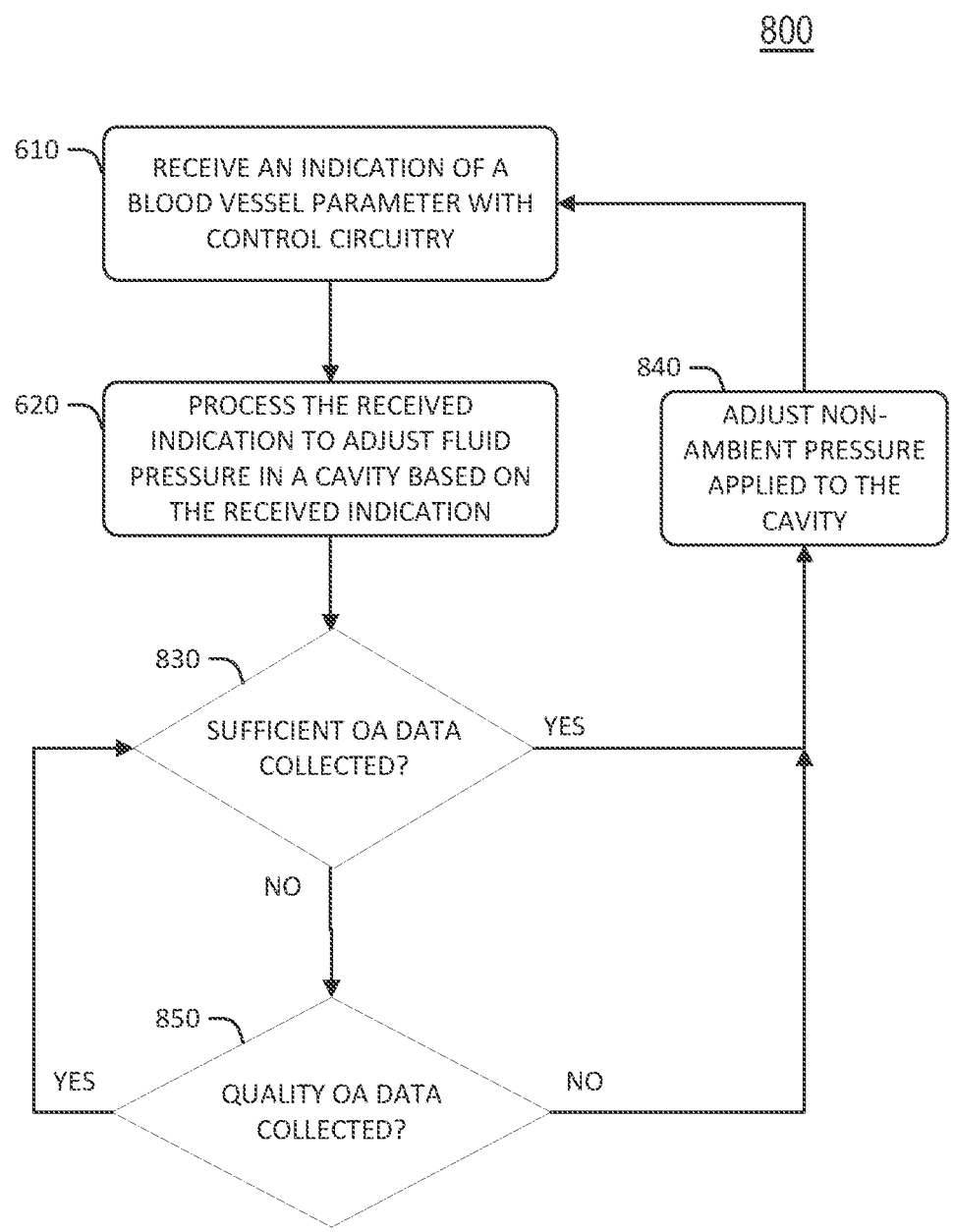
FIG. 8 shows an example method for using the apparatus to quantify OA capability of a patient eye.

FIG. 8 shows an example method 800 for using the apparatus 100 to quantify OA capability of a patient eye. In an example, the control circuitry 140 can collect OA value data to form an OA capability line, such as to estimate an OA index.

At 610, receiving the indication can include receiving an indication of a blood vessel parameter, such as an indication of blood flow in an ocular blood vessel. Receiving an indication can include receiving an indication of IOP in the patient eye and an indication of systemic BP in the patient.

At 620, processing the received indication can include forming the OA value, such as an ordered pair of indication data, including received or calculated indication data. The OA value can include an independent variable, such as an indication of OPP level, and a dependent variable, such as an indication of blood flow level in the ocular blood vessel associated with the indication of OPP.

Processing the indication can include calculating a parameter of the OA capability line. A parameter of the OA capability line can include the slope of the OA capability line, such as the slope of a best-fit line between at least two OA values. A parameter of the OA capability line can a length of the OA capability line, such as the length of the OA capability line with a specified slope. The length of the OA capability line can include the length of the OA plateau on the OA capability line between a first independent value and a second independent value. In an example, the length of the OA capability line can vary based on the slope of the OA capability line, such as between the first and second independent values of the OA capability graph.

Calculating the slope of an OA capability line can include calculating a spline, such as based upon two or more OA values. In an example, a first OA value and a second OA value can define a two-point spline, such as a straight line connecting the first and second OA values. The slope of the two-point spline can define an OA index to quantify OA capability in the eye. An additional OA value, such as a third OA value, can be combined with the first and second OA values to define a three-point spline, such as a mathematical expression representing a piecewise smooth curve between the first, second, and third OA values. The slope of the three-point spline can be defined as at least one of an arithmetic average of the piecewise smooth curve slopes or the slope of a best-fit line through the first, second, and third OA values defined in a least mean squares (LMS) sense.

At 830, the control circuitry 140 can determine the sufficiency of OA data collection. Determining sufficiency of OA data can include determining if enough OA values have been collected with the control circuitry 140 to estimate an OA index. In an example, at least two OA values can be collected, such as to define a line from which a slope can be calculated to define the OA index. In an example, a user can specify the number of OA values for collection to calculate the OA index.

Determining sufficiency of OA data can include averaging two or more dependent variables associated with a specified independent variable. In an example, the arithmetic mean of two or more indication of blood flow associated with a specified indication of OPP can be determined, such as to enhance the accuracy of the resultant OA value.

At 840, the control circuitry 140 can adjust the non-ambient pressure applied to the cavity 112, such as from a first non-ambient pressure to a second non-ambient pressure. Adjusting the non-ambient pressure applied to the cavity can include incrementally adjusting the non-ambient pressure applied to the cavity based upon a received indication of pressure level associated with the eye, such as an indication of pressure level in the cavity 112 (e.g., cavity pressure) or an indication of IOP level in the eye. The second non-ambient pressure level applied to the cavity 112, such as an incremental pressure level to adjust the first non-ambient pressure level, can be based upon the received first non-ambient pressure level, such as the second non-ambient pressure level can be a function of the received first pressure level. For example, the second non-ambient pressure level applied to the cavity 112 can be a function of the difference between the first non-ambient pressure level and a target level or a percentage of the first non-ambient pressure level.

Adjusting the non-ambient pressure applied to the cavity can include adjusting the non-ambient pressure applied to the cavity based upon a percentage multiple of the received indication of pressure level. The percentage multiple can include a predetermined percentage multiple, such as 1%, 2%, 3%, 5%, 10%, 20%, 30% of the received indication of pressure level. The second non-ambient pressure applied to the cavity 112 can be based upon a percentage multiple of the received first pressure level. In an example, when the predetermined percentage multiple can be about 25%, the second non-ambient pressure can be about 75% to about 125% of the received indication of the first pressure level, such as the first TOP level. In an example, when the predetermined percentage multiple can be about 10%, the second non-ambient pressure can be about 90% to about 110% of the received indication of the first pressure level, such as the first TOP level.

At 850, the control circuitry 140 can compare the collected ordered pairs to a target criterion, such as to determine if the calculated OA index can meet a set of metrics to ensure data quality and integrity. For example, the received indication of pressure level can include extraneous data, such as data that do not reflect the true nature of the sensed pressure level. In an example, sensing of pressure level data, such as TOP level data, can be confounded by events unrelated to the sensed data, such as the patient rubbing the eye during operation of the apparatus 100. To mitigate the impact of confounding events, the apparatus 100 can compare ordered pair data, such as at least one of pressure level data and OA index data, to a quality criterion, such as with the control circuitry 140.

Comparing ordered pair data to a criterion can include comparing an indication of calculated OA index, such as the slope of a two-point spline, to a predetermined slope value. In an example, the slope of the two-point spline can be compared to a predetermined slope value, such as an indication of slope from a predetermined reference point including the positive horizontal axis of a Cartesian coordinate system.

Knowledge of pressure in the body, such as intracranial pressure level including cerebrospinal fluid pressure (CSFP) level, can be of great interest in the diagnosis or treatment of an eye condition. The CSFP level in a patient can be measured by lumbar puncture, such as a medical procedure where a needle is inserted into the spinal canal of a patient to perform intracranial pressure monitoring. However, lumbar puncture is an invasive procedure that can result in complications, such as headache, nausea, and paralysis.

A spontaneous venous pulsation (SVP) is a subtle, periodic variation in the caliber of a retinal blood vessel that can occur in the eye of the patient, such as due to a pressure gradient between an intraocular retinal vein and a retrolaminar portion of the central retinal vein. The retinal blood vessel can remain patent, such as when the venous intraluminal pressure exceeds the IOP and CSFP in the patient. Ocular pulse pressure (e.g., the variation between systolic and diastolic intraocular venous pressure) can ordinarily be greater than cerebrospinal fluid (CSF) pulse pressure, such as ocular blood flow from the eye can increase during systole and decrease or experience retrograde flow during diastole. As ocular pulse pressure equilibrates with CSF pulse pressure, such as the condition where IOP in the patient eye can equilibrate with venous intraluminal pressure, the retinal blood vessel can collapse, such as to extinguish the SVP. The pressure level at extinguishment of the SVP, such as at least one of cavity pressure level or IOP level that extinguishes SVP, can indicate an equilibrium between IOP, venous intraluminal pressure, and CSFP, such as the IOP level at equilibrium can approximate, or become a surrogate for, CSFP in the patient.

The SVP in the eye can be described by a parameter, such as an SVP state parameter (or SVP state) including a binary SVP state. The binary SVP state can include an SVP ON state, such as where the sensor 130 can detect an indication of a change in a blood vessel parameter over a period of time, such as the duration of a patient cardiac cycle. A cardiac cycle can include the process of relaxation (diastole) and contraction (systole) of the heart muscle required to perfuse the body. A change in a blood vessel parameter can include at least one of a change in vessel caliber or a change in blood flow in the vessel. The binary SVP state can include an SVP OFF state, such as where the sensor can detect an absence of change in a blood vessel parameter over the duration of a patient cardiac cycle. A target SVP state can include a transition state, such as a transition state from a first SVP state to a second SVP state including at least one of an SVP ON state to an SVP OFF state or an SVP OFF state to an SVP ON state. A transition state can include the state where IOP is approximately equal to (or otherwise equilibrated with) CSFP in the patient.

A target SVP state can be defined by the state of a blood vessel parameter, such as blood flow in a blood vessel. In an example, an SVP ON state can include a blood vessel experiencing blood flow in the vessel, such as blood flow in the vessel greater than about 0 ml/sec, and an SVP OFF state can include a blood vessel experienced no blood flow in the vessel, such as blood flow in the vessel of about 0 ml/sec.

The SVP state in the patient eye can be adjusted, such as to a target SVP state including a transition SVP state, by adjusting the non-ambient pressure applied to the anterior surface of the patient eye. In adjusting non-ambient applied pressure to the eye, IOP in the patient eye can be adjusted, such as increased or decreased, to equilibrate IOP with CSFP in the patient. Upon achieving the target SVP state, the IOP in the patient eye can serve as a surrogate of CSFP in the patient.

The apparatus 100 can include a CSFP apparatus (or CFSPA), such as to non-invasively measure a physiological pressure level in a patient including a CSFP level in the patient. The CSFPA can include a cover 110, a fluid regulator 120, a sensor 130, control circuitry 140, and a pressure source 150.

The sensor 130 can include an SVP sensor, such as a sensor configured to sense an indication of a blood vessel parameter. The blood vessel parameter can include a change in vessel caliber, such as an indication of dynamic vessel caliber variation in an ocular blood vessel. The dynamic vessel caliber variation can be related to a physiological parameter, such as ocular pulse pressure. The SVP sensor can include a pressure-based sensor, such as a pressure sensor located in fluidic communication with the cavity 112 and configured to sense dynamic variations in cavity pressure, such as due to the motion of the cornea in response to pulsations of ocular blood vessels including motion correlated with ocular pulse pressure. The SVP sensor can include a strain-based sensor, such as a strain sensor integrated into an ocular contact lens and configured to sense dynamic variations in at least one of corneal or scleral displacement, such as due to intraocular volume changes correlated with ocular pulse pressure. In an example, a strain-based SVP sensor can include a contact lens-based sensor from Sensimed AG (Lausanne, Switzerland) offered for sale under the trademark SENSIMED TRIGGERFISH®.

The control circuitry 140 can be configured to process an estimate of cerebrospinal fluid pressure based on a blood vessel parameter, such as an indication of vessel caliber including an SVP. The control circuitry 140 can receive an indication of a blood vessel parameter from an ocular blood vessel and process the received indication, such as to adjust fluid pressure in the cavity 112 based on the received indication.

The control circuitry 140 can include a CPU configured as a feedback control circuit, such as to generate a control signal for the pressure source 150 (e.g., a pressure source control signal), to adjust pressure level in the cavity 112, such as based on the received indication of the blood vessel parameter. The received indication can include at least one of an indication of blood flow in the blood vessel, such as sensed by a blood flow sensor, or an indication of vessel caliber, such as sensed by an imaging sensor or an SVP sensor. The imaging sensor can sense and capture one or more retinal images including one or more retinal vessels over a duration of time, such as a patient cardiac cycle. In an example, the control circuitry 140 can be configured to adjust pressure in the cavity 112 toward changing TOP level in the patient eye to achieve a target level, such as a target TOP level in the patient eye. In an example, the control circuitry 140 can be configured to adjust pressure in the cavity 112 toward changing a target state of the eye, such as adjusting pressure in the cavity 112 to adjust TOP level in the eye toward a target SVP state including a transition state.

The CPU can execute a CSFP pressure source adjustment cycle, such as series of actions to adjust the SVP state in the eye. In an example of the CSFP pressure source adjustment cycle, the anterior surface of the eye can experience an initial pressure applied to the cavity 112, such as a non-ambient pressure. The control circuitry 140 can receive a first indication of a blood vessel parameter, such as associated with a first BP including a diastolic BP in a patient cardiac cycle, and a second indication of the blood vessel parameter, such as associated with a second BP including the concomitant systolic BP in the patient cardiac cycle. The CPU can compare the first indication to the second indication, such as to determine whether a target criterion has been achieved. If the target criterion has been achieved, the CPU can display the initial pressure applied to the cavity 112, such as an estimate of CSFP in the patient. If the target criterion has not been achieved, the control circuitry 140 can incrementally adjust the initial pressure applied to the cavity 112 toward achievement of the target criterion, such as to increase or decrease the pressure applied to the cavity 112. The pressure source adjustment cycle can be executed multiple times, such as to incrementally adjust pressure in the cavity 112 until the target criterion has been achieved.

The target criterion can include a target CSFP blood flow level, such as an ocular blood flow level selected to indicate equilibrium between the TOP, intraluminal pressure, and CSFP in a patient. The target CSFP blood flow level in an ocular blood vessel can vary, such as depending on the diameter of the blood vessel. In an example, the target CSFP blood flow level can include a range of blood flow, such as a range from about 5 µl/min to about zero (or null) flow of blood in the ocular vessel.

The target criterion can include a target CSFP vessel factor. The target CSFP vessel factor can include at least one of a vessel caliber factor or a vessel characteristic factor. The vessel factor can be a function of an indication of a blood vessel parameter, such as at least one of blood vessel flow, vessel caliber, or vessel shape. The blood vessel parameter can be sensed by the sensor 130, such as an imaging sensor, and subsequently captured, such as for processing with the control circuitry 140.

A vessel caliber factor can quantify a change in a blood vessel parameter, such as a change in vessel caliber between a first and second image at a specific pressure applied to the anterior surface of the patient eye. A vessel caliber factor can describe the state of collapse of a blood vessel subjected to a specified pressure applied to the anterior surface of the eye. In an example, a target vessel caliber factor can include a range of values, such as at least one of a range from about 0.6 to about 0.7, a range from about 0.7 to about 0.8, or a range from about 0.8 to about 0.9. A target vessel caliber factor of about .63 can indicate complete collapse of the vessel, such as at least a portion of the vessel tunica intima can be in contact with another portion of the vessel tunica intima.

The vessel caliber factor can be defined as a ratio of a first vessel caliber value and a second vessel caliber value of a blood vessel, such as a blood vessel subjected to a specific pressure applied to the anterior surface of the eye. In an example, a first vessel caliber value can include the major axis of vessel caliber in a first image corresponding to a first blood pressure level at the specific applied pressure, and a second vessel caliber value can include the major axis of vessel caliber in a second image corresponding to a second blood pressure level at the specific applied pressure. In an example, the first blood pressure level can correspond to a systolic blood pressure level in the patient and the second blood pressure level can correspond to a concomitant diastolic blood pressure level.

A vessel characteristic factor to quantify a change in a blood vessel parameter, such as a change in vessel cross-sectional shape between a first and second image at a specific pressure applied to the anterior surface of the patient eye. A vessel characteristic factor can describe the state of circular deformation of a blood vessel subjected to a specified pressure applied to the anterior surface of the eye. In an example, a target vessel characteristic factor can include a range of values, such as at least one of a range from about 100 to about 1,000, a range from about 1,000 to about 10,000, or a range from about 10,000 to about 100,000.

The blood vessel characteristic factor can be defined as a ratio of a first blood vessel shape characteristic, such as the ratio of the major axis of the blood vessel and the minor axis of the blood vessel in the first image corresponding to a first blood pressure level, and a second blood vessel shape characteristic, such as the ratio of the major axis of the blood vessel and the minor axis of the blood vessel in the first image corresponding to a first blood pressure level. In an example, the first blood pressure level can correspond to a systolic blood pressure level in the patient and the second blood pressure level can correspond to a concomitant diastolic blood pressure level.

Figure 9:
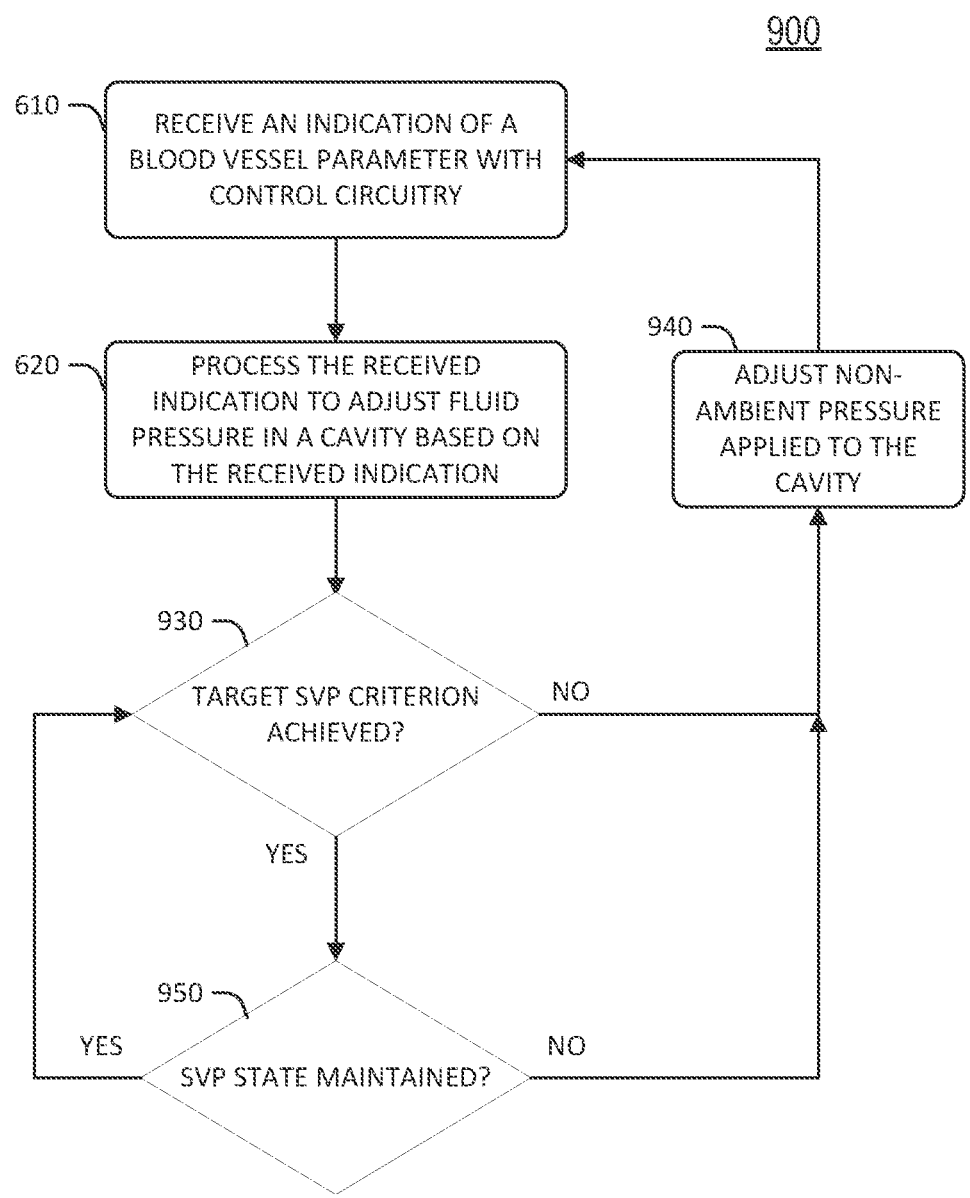
FIG. 9 shows an example method for using the apparatus to non-invasively detect CSFP level in a patient.

FIG. 9 shows an example method 900 for using the apparatus 100 to non-invasively detect CSFP level in a patient. The control circuitry 140 can be configured to receive an indication of an SVP from a blood vessel in the eye and process the received indication to adjust fluid pressure in the cavity 112 based on received indication. In an example, the control circuitry 140 can adjust the SVP state, such as from a first SVP state to a second SVP state, to estimate CSFP level in the patient.

At 610, an indication of a blood vessel parameter can be received with the control circuitry 140. Receiving the indication can include receiving an indication of SVP including an indication of SVP state, such as from an ocular blood vessel. In an example, receiving the indication can include capturing a retinal image, such as one or more retinal images, over a single cardiac cycle. Receiving an indication can include receiving an indication of IOP in the patient eye and an indication of systemic BP in the patient.

At 620, processing the received indication of the blood vessel can be processed with the control circuitry 140. Processing the received indication can include determining the SVP state, such the binary SVP state including at least one of SVP ON or SVP OFF. SVP state can be determined, such as by using the steps as associated with the CSFP pressure source adjustment cycle described in this application. An ocular blood vessel parameter can include at least one of vessel caliber, vessel shape, vessel color, or vessel blood flow, such as at least one of volume or velocity. A change in a vessel parameter during a patient cardiac cycle can characterize an SVP ON state. The absence of change in a vessel parameter can characterize an SVP OFF state.

At 930, achievement of a target criterion, including a target SVP criterion, can be identified. The target SVP criterion can include a transition SVP criterion, such as transition from a first binary SVP state to a second binary SVP state, to inform a user the indication of IOP can approximate the indication of CSFP. The transition SVP state can include at least one of a change from the SVP ON state to the SVP OFF state or from the SVP OFF state to the SVP ON state. Identifying achievement of the target SVP criterion can include comparing a first SVP state to a second SVP state, such as to determine equivalency of the SVP states. In an example, the transition SVP criterion can be satisfied, such as when the first binary SVP state is not equivalent to the second binary SVP state.

At 940, the non-ambient pressure level applied to the cavity 112 can be adjusted. Adjusting the non-ambient pressure level can include incrementally adjusting the non-ambient pressure level. An incremental adjustment can include at least one of a fixed increment pressure adjustment, such as defined by a user, or a percentage of the fixed increment pressure adjustment based on an indication of a blood vessel parameter.

Incrementally adjusting can include calculating the difference between a first and second received vessel parameter and generating a pressure source control signal based on a percentage of the calculated difference. As an illustration, a small difference between the first and second received vessel parameters can imply a large difference between IOP and CSFP, such as non-ambient pressure adjustment increments applied to the cavity 112 can be relatively large, such as to achieve the transition SVP state more quickly. In an example, where the difference in the first and second blood vessel parameter exists in a range of about 0% to about 25% of the first blood vessel parameter value, the fixed increment pressure adjustment can be modified by a multiplier in a range of about 1× to about 5×.

A large difference between the first and second received vessel parameters can imply a small difference between IOP and CSFP, such as non-ambient pressure adjustment increments applied to the cavity 112 can be relatively small, such as to more accurately estimate CSFP based on the achievement of the transition SVP state. In an example, where the difference in the first and second blood vessel parameter exists in a range of about 25% to about 99% of the first received vessel parameter, the fixed increment pressure adjustment can be modified by a multiplier in a range of about 0.01× to about 1×.

At 950, maintenance of a target criterion, including a target SVP criterion, can be identified. Identifying maintenance of the target SVP criterion can include comparing a first SVP state to a second SVP state, such as to determine equivalency of the SVP states. In an example, the transition SVP criterion can be maintained, such as when the first binary SVP state is equivalent to the second binary SVP state.

VARIOUS NOTES

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An apparatus to adjust an indication of ocular perfusion pressure (OPP) in an eye of a patient, the indication of OPP including a relationship between an indication of systemic blood pressure in the patient and an indication of intraocular pressure (IOP) in the patient eye, the apparatus comprising:
a cover, sized and shaped to fit over the eye to define a cavity between the cover and an anterior surface of the eye;
a pressure source, in communication with the cavity, configured to adjust fluid pressure in the cavity to affect the indication of OPP; and
control circuitry, in communication with the pressure source, configured to receive the indication of systemic blood pressure and the indication of IOP, calculate the indication of OPP, and adjust the pressure source to change fluid pressure in the cavity to move the indication of OPP toward a target OPP in the patient eye.

2. The apparatus of claim 1, wherein the control circuitry is configured to change the fluid pressure in the cavity toward the target OPP based at least in part on at least one of the indication of systemic blood pressure in the patient or the indication of IOP in the patient eye.

3. The apparatus of claim 2, wherein the control circuitry is configured to change the fluid pressure in the cavity to move the indication of OPP toward the target OPP based on a difference between the indication of systemic blood pressure and the indication of IOP.

4. The apparatus of claim 2, wherein the control circuitry is configured to change the fluid pressure in the cavity to move the indication of OPP toward the target OPP based on mean ocular perfusion pressure (MOPP).

5. The apparatus of claim 1, wherein the control circuitry is configured to adjust the fluid pressure in the cavity to move the indication of OPP toward a target IOP level.

6. The apparatus of claim 5, wherein the control circuitry is configured to adjust the fluid pressure in the cavity to move the indication of OPP toward a target IOP level based at least in part on at least one of the indication of IOP and the indication of OPP.

7. The apparatus of claim 1, wherein the control circuitry is configured to receive an indication of blood flow in the patient eye associated with the indication of OPP to generate an ocular autoregulation (OA) value.

8. The apparatus of claim 7, wherein the control circuitry is configured to adjust the fluid pressure in the cavity to move the indication of OPP toward a target level, wherein the target level includes a target OPP graph-point level and the control circuitry is configured to generate the OA value as an OA ordered pair including the target OPP graph-point level and the indication of blood flow corresponding to the target OPP graph-point level.

9. The apparatus of claim 8, wherein the control circuitry is configured to process at least two OA ordered pairs to calculate an OA index.

10. The apparatus of claim 9, wherein the OA index includes a slope of a best-fit line between at least two OA ordered pairs.

11. The apparatus of claim 1, wherein the control circuitry is configured to adjust the fluid pressure in the cavity to move the indication of OPP toward a target SVP state including a transition SVP state to estimate CSFP level in the patient.

12. The apparatus of claim 11, wherein the control circuitry is configured to receive an indication of systemic blood pressure including an indication of at least one of systolic blood pressure level or diastolic blood pressure level, and
wherein the control circuitry is configured to capture at least one of a first image of a blood vessel parameter corresponding to the systolic blood pressure level or a second image of the blood vessel parameter corresponding to a diastolic blood pressure level.

13. The apparatus of claim 1, wherein the target OPP includes a target OPP range from about 30 mmHg to about 70 mmHg.

14. The apparatus of claim 1, wherein the target OPP includes a target OPP range from about 40 mmHg to about 60 mmHg.

15. The apparatus of claim 1, wherein the target OPP includes a target OPP range from about 45 mmHg to about 55 mmHg.

16. A method to adjust an indication of ocular perfusion pressure (OPP) in a patient eye using an apparatus, the apparatus comprising a cover, sized and shaped to fit over the eye to define a cavity between an interior surface of the cover and an anterior surface of the eye, a pressure source, in communication with the cavity, configured to adjust fluid pressure in the cavity to affect the indication of OOP, and control circuitry, in communication with the pressure source, configured to adjust the pressure source to change fluid pressure in the cavity to move the indication of OPP toward a target OPP in the patient eye, the method comprising:

receiving an indication of systemic blood pressure in the patient and an indication of intraocular pressure (IOP) in the patient eye with the control circuitry;

calculating the indication of OPP from the received indications of systemic blood pressure and IOP with the control circuitry; and adjusting the pressure source to change fluid pressure in the cavity to move the indication of OPP toward a target OPP in the patient eye.

17. The method of claim 16, wherein adjusting the pressure source toward a target OPP includes applying negative non-ambient gauge pressure to the cavity.

18. The method of claim 16, wherein adjusting the pressure source to move the indication of OPP toward a target OPP includes applying positive non-ambient gauge pressure to the cavity.

19. The method of claim 16, wherein adjusting the pressure source to move the indication of OPP toward a target OPP includes adjusting pressure in the cavity based at least in part on at least one of the indication of systemic blood pressure in the patient or the indication of IOP in the patient eye.

20. The method of claim 16, wherein adjusting the pressure source to move the indication of OPP toward a target OPP includes applying non-ambient pressure in the cavity to achieve a target OPP in a range of about 30 mmHg to about 70 mmHg.

* * * * *